US006455492B1

(12) United States Patent
Reyes et al.

(10) Patent No.: US 6,455,492 B1
(45) Date of Patent: Sep. 24, 2002

(54) HEPATITIS E VIRUS VACCINE AND METHOD

(75) Inventors: Gregory R. Reyes, Palo Alto, CA (US); Daniel W. Bradley, Lawrenceville, GA (US); Jr-Shin Twu, Daly City, CA (US); Michael A. Purdy, Atlanta, GA (US); Albert W. Tam, San Francisco, CA (US); Krzysztof Z. Krawczynski, Tucker, GA (US); Patrice O. Yarbough, Union City, CA (US)

(73) Assignee: Genelabs Technologies, Inc., Redwood City, CA (US)

( * ) Notice: Subject to any disclaimer, the term of this patent is extended or adjusted under 35 U.S.C. 154(b) by 0 days.

(21) Appl. No.: 07/870,985

(22) Filed: Apr. 20, 1992

Related U.S. Application Data

(63) Continuation-in-part of application No. 07/822,335, filed on Jan. 17, 1992, now abandoned, which is a continuation-in-part of application No. 07/505,888, filed on Apr. 5, 1990, now abandoned, which is a continuation-in-part of application No. 07/420,921, filed on Oct. 13, 1989, now abandoned, which is a continuation-in-part of application No. 07/367, 486, filed on Jun. 16, 1989, now abandoned, which is a continuation-in-part of application No. 07/336,672, filed on Apr. 11, 1989, now abandoned, which is a continuation-in-part of application No. 07/208,997, filed on Jun. 17, 1988, now abandoned.

(51) Int. Cl.[7] .......................... A01N 37/18; C12Q 1/70; C07K 16/00

(52) U.S. Cl. ........................... 514/2; 435/5; 435/235.1; 530/387.1; 530/388.3; 530/388.35

(58) Field of Search ................ 435/5, 235.1; 424/93 A, 424/93 R, 93 T, 85.8, 86; 530/388.3, 388.35, 826, 350, 387.1; 930/220, 221, 223; 514/2

(56) References Cited

U.S. PATENT DOCUMENTS 4,871,659 A * 10/1989 Pillot ............................ 435/5
5,202,430 A * 4/1993 Brian et al. .............. 536/23.72
5,218,099 A * 6/1993 Reyes et al. ............. 536/23.72

FOREIGN PATENT DOCUMENTS

| | | |
|---|---|---|
| JP | 4200388 | * 7/1992 |
| WO | 9115603 | * 10/1991 |

OTHER PUBLICATIONS

Cohen, "Immunization", p. 703–706, *Bosie and Clinical Immunology*, Stites et al., eds., 1982, Lange Medical Publications, Los Altos, California.*

Bradley et al., *PN.A.S., U.S.A.*, vol. 84, pp. 6277–6281, Sep. 1987.*

Purdy, et al., *Archives of Virology*, vol. 123, pp. 335–349, 1992.*

Sequence Comparison—Computer Generated.*

Tam et al, *Virology*, 185:120–131 (1991).

Huang et al, *Virology*, :1–9 (1992).

Bradley et al, *Proc. Natl. Acad. Sci. USA*, 84:6277–6281 (1987).

Purdy et al, *Arch Virol*, 123:335–349 (1992).

Yarbough et al, *J. Virology*, 65:5790–5797 (1991).

Reyes et al, *Reports*, :1335–1339 (1990).

* cited by examiner

*Primary Examiner*—B. L. Sisson
(74) *Attorney, Agent, or Firm*—Perkins Coie LLP

(57) ABSTRACT

Antigen and antibody vaccine composition effective in preventing hepatitis E virus (HEV) infection are disclosed. The antigen composition includes peptides corresponding to carboxyl terminal end regions of the second and third open reasing frames of the HEV genome. The composition is effective in preventing HEV infection after vaccination. The antibody composition contains an antibody effective to block HEV infection of human primary hepatocytes in culture.

5 Claims, 11 Drawing Sheets

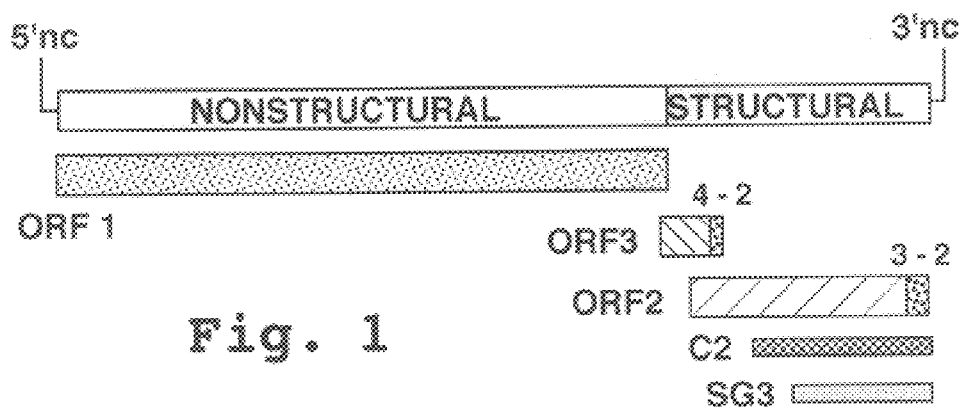
Fig. 1
Fig. 4    551 bp →
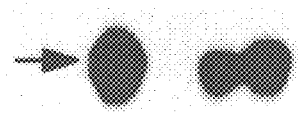
Fig. 5    448 bp →
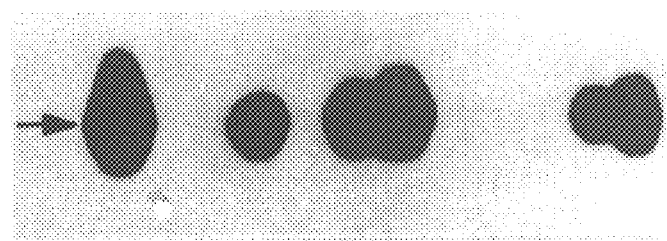
448 bp →
Fig. 6

```
        |--ORF3-->                              |--ORF2-->
        ↓                                       ↓
    5110v     5120v      5130v     5140v     5150v      5160v
TGGAATGAATAACATGTCTTTTGCTGCGCCCATGGGTTCGCGACCATGCGCCCTCGGCCT
  GAATGAATAACATGT    TTTGCTGCGCCCATGGGTTCGC ACCATGCGCCCT GGCCT
CTGAATGAATAACATGTGGTTTGCTGCGCCCATGGGTTCGCCACCATGCGCCCTAGGCCT 5170v     5180v     5190v     5200v     5210v     5220v
ATTTTGTTGCTGCTCCTCATGTTTTTGCCTATGCTGCCCGCGCCACCGCCCGGTCAGCCG
  TTTTG TG TG TCCTC TGTTT TGCCTATG TGCCCGCGCCACCG CCGGTCAGCCG
CTTTTGCTGTTGTTCCTCTTGTTTCTGCCTATGTTGCCCGCGCCACCGACCGGTCAGCCG 5230v     5240v     5250v     5260v     5270v     5280v
TCTGGCCGCCGTCGTGGGCGGCGCAGCGGCGGTTCCGGCGGTGGTTTCTGGGGTGACCGG
TCTGGCCGCCGTCGTGGGCGGCGCAGCGGCGGT CCGGCGGTGGTTTCTGGGGTGACCGG
TCTGGCCGCCGTCGTGGGCGGCGCAGCGGCGGTACCGGCGGTGGTTTCTGGGGTGACCGG 5290v     5300v     5310v     5320v     5330v     5340v
GTTGATTCTCAGCCCTTCGCAATCCCCTATATTCATCCAACCAACCCCTTCGCCCCCGAT
GTTGATTCTCAGCCCTTCGCAATCCCCTATATTCATCCAACCAACCCCTT GCCCC GA
GTTGATTCTCAGCCCTTCGCAATCCCCTATATTCATCCAACCAACCCCTTTGCCCCAGAC

|--406.4-2-->
                                    ↓
    5350v     5360v     5370v     5380v     5390v     5400v
GTCACCGCTGCGGCCGGGGCTGGACCTCGTGTTCGCCAACCCGCCCGACCACTCGGCTCC
GT   CCGCTGCG CCGGG CTGGACCTCG TTCGCCAACC GCCCG CCACT GGCTCC
GTTGCCGCTGCGTCCGGGTCTGGACCTCGCCTTCGCCAACCAGCCCGGCCACTTGGCTCC 5410v     5420v     5430v     5440v     5450v     5460v
GCTTGGCGTGACCAGGCCCAGCGCCCCGCCGTTGCCTCACGTCGTAGACCTACCACAGCT
  CTTGGCG GA CAGGCCCAGCGCCCC CCG TGCCTC CGTCG  GACCT CCACAGC
ACTTGGCGAGATCAGGCCCAGCGCCCCTCCGCTGCCTCCCGTCGCCGACCTGCCACAGCC

<--406.4-2--|
        <-ORF3-↓
    5470v     5480v     5490v     5500v     5510v     5520v
GGGGCCGCGCCGCTAACCGCGGTCGCTCCGGCCCATGACACCCCGCCAGTGCCTGATGTC
GGGGC GCG CGCT AC GC GT GC CC GCCCATGACACC C CC GT CC GA GT
GGGGCTGCGGCGCTGACGGCTGTGGCGCCTGCCCATGACACCTCACCCGTCCCGGACGTT 5530v     5540v     5550v     5560v     5570v     5580v
GACTCCCGCGGCGCCATCTTGCGCCGGCAGTATAACCTATCAACATCTCCCCTTACCTCT
GA TC CGCGG GC AT   T CGCCG CAGTATAA  T TC AC TC CCCCT AC TC
GATTCTCGCGGTGCAATTCTACGCCGCCAGTATAATTTGTCTACTTCACCCCTGACATCC
```

Fig. 7A

```
         5590v      5600v      5610v      5620v      5630v      5640v
      TCCGTGGCCACCGGCACTAACCTGGTTCTTTATGCCGCCCCTCTTAGTCCGCTTTTACCC
      TC GTGGCC  C GGCACTAA   T GT CT TATGC GCCCC  CTTA TCCGC T T CC
      TCTGTGGCCTCTGGCACTAATTTAGTCCTGTATGCAGCCCCCCTTAATCCGCCTCTGCCG 5650v      5660v      5670v      5680v      5690v      5700v
      CTTCAGGACGGCACCAATACCCATATAATGGCCACGGAAGCTTCTAATTATGCCCAGTAC
      CT CAGGACGG AC AATAC CA AT ATGGCCAC GA GC TC AATTATGC CAGTAC
      CTGCAGGACGGTACTAATACTCACATTATGGCCACAGAGGCCTCCAATTATGCACAGTAC 5710v      5720v      5730v      5740v      5750v      5760v
      CGGGTTGCCCGTGCCACAATCCGTTACCGCCCGCTGGTCCCCAATGCTGTCGGCGGTTAC
      CGGGTTGCCCG GC AC ATCCGTTACCG CC CT GT CC AATGC GT GG GG TA
      CGGGTTGCCCGCGCTACTATCCGTTACCGGCCCCTAGTGCCTAATGCAGTTGGAGGCTAT (C2) ↓→

5770v      5780v      5790v      5800v      5810v      5820v
      GCCATCTCCATCTCATTCTGGCCACAGACCACCACCACCCCGACGTCCGTTGATATGAAT
      GC AT TCCAT TC TTCTGGCC CA AC ACCAC ACCCC AC TC GTTGA ATGAAT
      GCTATATCCATTTCTTTCTGGCCTCAAACAACCACAACCCCTACATCTGTTGACATGAAT 5830v      5840v      5850v      5860v      5870v      5880v
      TCAATAACCTCGACGGATGTTCGTATTTTAGTCCAGCCCGGCATAGCCTCTGAGCTTGTG
      TC AT AC TC AC GATGT  G ATT T GT CA CC GGCATAGC CTGA   T GT
      TCCATTACTTCCACTGATGTCAGGATTCTTGTTCAACCTGGCATAGCATCTGAATTGGTC 5890v      5900v      5910v      5920v      5930v      5940v
      ATCCCAAGTGAGCGCCTACACTATCGTAACCAAGGCTGGCGCTCCGTCGAGACCTCTGGG
      ATCCCAAG GAGCGCCT CACTA CG AA CAAGG TGGCGCTC GT GAGAC TCTGG
      ATCCCAAGCGAGCGCCTTCACTACCGCAATCAAGGTTGGCGCTCGGTTGAGACATCTGGT 5950v      5960v      5970v      5980v      5990v      6000v
      GTGGCTGAGGAGGAGGCTACCTCTGGTCTTGTTATGCTTTGCATACATGGCTCACTCGTA
      GT GCTGAGGAGGA GC ACCTC GGTCTTGT ATG T TGCATACATGGCTC C  GT
      GTTGCTGAGGAGGAAGCCACCTCCGGTCTTGTCATGTTATGCATACATGGCTCTCCAGTT 6010v      6020v      6030v      6040v      6050v      6060v
      AATTCCTATACTAATACACCCTATACCGGTGCCCTCGGGCTGTTGGACTTTGCCCTTGAG
      AA TCCTATAC AATAC CC TATACCGGTGCCCT GG  T TGGACTTTGCC T GAG
      AACTCCTATACCAATACCCCTTATACCGGTGCCCTTGGCTTACTGGACTTTGCCTTAGAG 6070v      6080v      6090v      6100v      6110v      6120v
      CTTGAGTTTCGCAACCTTACCCCCGGTAACACCAATACGCGGGTCTCCCGTTATTCCAGC
      CTTGAGTTTCGCAA CT ACC CC GTAACACCAATAC CG GT TCCCGTTA TCCAGC
      CTTGAGTTTCGCAATCTCACCACCTGTAACACCAATACACGTGTGTCCCGTTACTCCAGC
```

```
      6130v        6140v        6150v        6160v        6170v        6180v
ACTGCTCGCCACCGCCTTCGTCGCGGTGCGGACGGGACTGCCGAGCTCACCACCACGGCT
ACTGCTCG CAC  C   CG  G G      GACGGGACTGC GAGCT ACCAC AC GC
ACTGCTCGTCACTCCGCCCGAGGGGCC---GACGGGACTGCGGAGCTGACCACAACTGCA 6190v        6200v        6210v        6220v        6230v        6240v
GCTACCCGCTTTATGAAGGACCTCTATTTTACTAGTACTAATGGTGTCGGTGAGATCGGC
GC ACC G TT ATGAA GA CTC A TTTAC G  TAATGG GT GGTGA TCGGC
GCCACCAGGTTCATGAAGATCTCCACTTTACCGGCCTTAATGGGGTAGGTGAAGTCGGC 6250v        6260v        6270v        6280v        6290v        6300v
CGCGGGATAGCCCTCACCCTGTTCAACCTTGCTGACACTCTGCTTGGCGGCCTGCCGACA
CGCGGGATAGC CT AC  T  T AACCTTGCTGACAC CT CT GGCGG CT CCGACA
CGCGGGATAGCTCTAACATTACTTAACCTTGCTGACACGCTCCTCGGCGGGCTCCCGACA 6310v        6320v        6330v        6340v        6350v        6360v
GAATTGATTTCGTCGGCTGGTGGCCAGCTGTTCTACTCCCGTCCCGTTGTCTCAGCCAAT
GAATT ATTTCGTCGGCTGG GG CA CTGTT TA TCCCG CC GTTGTCTCAGCCAAT
GAATTAATTTCGTCGGCTGGCGGGCAACTGTTTTATTCCCGCCCGGTTGTCTCAGCCAAT 6370v        6380v        6390v        6400v        6410v        6420v
GGCGAGCCGACTGTTAAGTTGTATACATCTGTAGAGAATGCTCAGCAGGATAAGGGTATT
GGCGAGCC AC GT AAG T TATACATC GT GAGAATGCTCAGCAGGATAAGGGT TT
GGCGAGCCAACCGTGAAGCTCTATACATCAGTGGAGAATGCTCAGCAGGATAAGGGTGTT 6430v        6440v        6450v        6460v        6470v        6480v
GCAATCCCGCATGACATTGACCTCGGAGAATCTCGTGTGGTTATTCAGGATTATGATAAC
GC ATCCC CA GA AT GA CT GG A TC CGTGTGGT ATTCAGGATTATGA AAC
GCTATCCCCCACGATATCGATCTTGGTGATTCGCGTGTGGTCATTCAGGATTATGACAAC 6490v        6500v        6510v        6520v        6530v        6540v
CAACATGAACAAGATCGGCCGACGCCTTCTCCAGCCCCATCGCGCCCTTTCTCTGTCCTT
CA CATGA CA GATCGGCC AC CC TC CC GC CCATC CG CCTTT TCTGT CT
CAGCATGAGCAGGATCGGCCCACCCCGTCGCCTGCGCCATCTCGGCCTTTTTCTGTTCTC 6550v        6560v        6570v        6580v        6590v        6600v
CGAGCTAATGATGTGCTTTGGCTCTCTCTCACCGCTGCCGAGTATGACCAGTCCACTTAT
CGAGC AATGATGT CTTTGGCT TC CTCAC GC GCCGAGTATGACCAGTCCACTTA
CGAGCAAATGATGTACTTTGGCTGTCCCTCACTGCAGCCGAGTATGACCAGTCCACTTAC 6610v        6620v        6630v        6640v        6650v        6660v
GGCTCTTCGACTGGCCCAGTTTATGTTTCTGACTCTGTGACCTTGGTTAATGTTGCGACC
GG TC TC ACTGGCCC GTTTAT T TC GAC   GTGAC TTGGT AATGTTGCGAC
GGGTCGTCAACTGGCCCGGTTTATATCTCGGACAGCGTGACTTTGGTGAATGTTGCGACT 6670v        6680v        6690v        6700v        6710v        6720v
GGCGCGCAGGCCGTTGCCCGGTCGCTCGATTGGACCAAGGTCACACTTGACGGTCGCCCC
GGCGCGCAGGCCGT GCCCG TCGCT GA TGG CCAA GTCAC CT GACGG CG CCC
GGCGCGCAGGCCGTAGCCCGATCGCTTGACTGGTCCAAAGTCACCCTCGACGGGCGGCCC
```

Fig. 7C

```
        6730v      6740v      6750v      6760v      6770v      6780v
CTCTCCACCATCCAGCAGTACTCGAAGACCTTCTTTGTCCTGCCGCTCCGCGGTAAGCTC
CTC C AC   T   AGCA TA TC AAGAC TTCTTTGT CT CC CT CG GG AAGCTC
CTCCCGACTGTTGAGCAATATTCCAAGACATTCTTTGTGCTCCCCCTTCGTGGCAAGCTC 6790v      6800v      6810v      6820v      6830v      6840v
TCTTTCTGGGAGGCAGGCACAACTAAAGCCGGGTACCCTTATAATTATAACACCACTGCT
TC TT TGGGAGGC GGCACAAC AAAGC GG TA CCTTATAATTATAA AC ACTGCT
TCCTTTTGGGAGGCCGGCACAACAAAAGCAGGTTATCCTTATAATTATAATACTACTGCT 6850v      6860v      6870v      6880v      6890v      6900v
AGCGACCAACTGCTTGTCGAGAATGCCGCCGGGCACCGGGTCGCTATTTCCACTTACACC
AG GACCA   T CT   T GA AATGC GCCGG CA CGGGTCGC ATTTC AC TA ACC
AGTGACCAGATTCTGATTGAAAATGCTGCCGGCCATCGGGTCGCCATTTCAACCTATACC 6910v      6920v      6930v      6940v      6950v      6960v
ACTAGCCTGGGTGCTGGTCCCGTCTCCATTTCTGCGGTTGCCGTTTTAGCCCCCCACTCT
AC AG CT GG GC GGTCC GTC CCATTTCTGCGG  GC GTTTT GC CC C CTC
ACCAGGCTTGGGGCCGGTCCGGTCGCCATTTCTGCGGCCGCGGTTTTGGCTCCACGCTCC

↓--406.3-2-->
        6970v      6980v      6990v      7000v      7010v      7020v
GCGCTAGCATTGCTTGAGGATACCTTGGACTACCCTGCCCGCGCCCATACTTTTGATGAT
GC CT GC   TGCT GAGGATAC TT GA TA CC G   CG GC CA AC TTTGATGA
GCCCTGGCTCTGCTGGAGGATACTTTTGATTATCCGGGGCGGGCGCACACATTTGATGAC 7030v      7040v      7050v      7060v      7070v      7080v
TTCTGCCCAGAGTGCCGCCCCCTTGGCCTTCAGGGCTGCGCTTTCCAGTCTACTGTCGCT
TTCTGCCC  GA TGCCGC C  T GGCCT CAGGG TG GCTTTCCAGTC ACTGTCGCT
TTCTGCCCTGAATGCCGCGCTTTAGGCCTCCAGGGTTGTGCTTTCCAGTCAACTGTCGCT
                                               <--SG3
                                               <--406.3-2
                                               <--C2
        7090v      7100v      7110v      7120v      7130v      7140v
GAGCTTCAGCGCCTTAAGATGAAGGTGGGTAAAACTCGGGAGTTGTAGTTTATTTGCTTG
GAGCT CAGCGCCTTAA  T AAGGTGGGTAAAACTCGGGAGTTGTAGTTTATTTG  TG
GAGCTCCAGCGCCTTAAAGTTAAGGTGGGTAAAACTCGGGAGTTGTAGTTTATTTGGCTG 7150v       7160v                7170v      7180v      7190v
TGCCCCCCTTCTTTCTGTTGC---------TTATTTCTCATTTCTGCGTTCCGCGCTCCC
TGCCC  CCT CTT        TGC      TTATTTC   TTTCT GT CCGCGCTCCC
TGCCCACCTACTTATATCTGCTGATTTCCTTTATTTCCTTTTTCTCGGTCCCGCGCTCCC

<-I ORF2 v 7195
TGA
TGA
TGA
```

Fig. 7D

```
              10        20        30        40        50        60
     MNNMSFAAPMGSRPCALGLFCCCSSCFCLCCPRHRPVSRLAAVVGGAAAVPAVVSGVTGL
     X:::  :::::::.:::::::::::::::::::::::::::::::::::::::::::::
     MNNMWFAAPMGSPPCALGLFCCCSSCFCLCCPRHRPVSRLAAVVGGAAAVPAVVSGVTGL
              10        20        30        40        50        60
                                  ↓406.4-2-->
                  406.4-2       ↓
              70        80        90       100       110       120
     ILSPSQSPIFIQPTPSPPMSPLRPGLDLVFANPPDHSAPLGVTRPSAPPLPHVVDLPQLG
     ::::::::::::::: :.   :::::::.:::.:.: ::::  .::::::::.:.::: :
     ILSPSQSPIFIQPTPLPQTLPLRPGLDLAFANQPGHLAPLGEIRPSAPPLPPVADLPQPG
              70        80        90       100       110       120
     <--↓406.4-2
        ↓
     PRRZ
      ::X
     LRRZ
```

Fig. 8

```
              10        20        30        40        50        60
     MRPRPILLLLLMFLPMLPAPPPGQPSGRRRGRRSGGSGGGFWGDRVDSQPFAIPYIHPTN
     X:::::..:::..::::::::::::::::::::::::.::::::::::::::::::::
     MRPRPLLLLFLLFLPMLPAPPTGQPSGRRRGRRSGGTGGGFWGDRVDSQPFAIPYIHPTN
              10        20        30        40        50        60

70        80        90       100       110       120
     PFAPDVTAAAGAGPRVRQPARPLGSAWRDQAQRPAVASRRRPTTAGAAPLTAVAPAHDTP
     :::::::..::.:.:::.::::::::::::.:::::::::..:::::.::::::::::.
     PFAPDVAAASGSGPRLRQPARPLGSTWRDQAQRPSAASRRRPATAGAAALTAVAPAHDTS
              70        80        90       100       110       120

130       140       150       160       170       180
     PVPDVDSRGAILRRQYNLSTSPLTSSVATGTNLVLYAAPLSPLLPLQDGTNTHIMATEAS
     ::::::::::::::::::::::::::::.:::::::::::.:::::::::::::::::::
     PVPDVDSRGAILRRQYNLSTSPLTSSVASGTNLVLYAAPLNPPLPLQDGTNTHIMATEAS
             130       140       150       160       170       180

↓ C-2-->
             190       200       210       220       230       240
     NYAQYRVARATIRYRPLVPNAVGGYAISISFWPQTTTTPTSVDMNSITSTDVRILVQPGI
     ::::::::::::::::::::::::::::::::::::::::::::::::::::::::::::
     NYAQYRVARATIRYRPLVPNAVGGYAISISFWPQTTTTPTSVDMNSITSTDVRILVQPGI
             190       200       210       220       230       240

250       260       270       280       290       300
     ASELVIPSERLHYRNQGWRSVETSGVAEEEATSGLVMLCIHGSLVNSYTNTPYTGALGLL
     :::::::::::::::::::::::::::::::::::::::::::.::::::::::::::::
     ASELVIPSERLHYRNQGWRSVETSGVAEEEATSGLVMLCIHGSPVNSYTNTPYTGALGLL
             250       260       270       280       290       300

↓ SG3-->
             310       320       330       340       350       360
     DFALELEFRNLTPGNTNTRVSRYSSTARHRLRRGADGTAELTTTAATRFMKDLYFTSTNG
     ::::::::::::. ::::::::::::::. :::::::::::::::::::::::.::.::
     DFALELEFRNLTTCNTNTRVSRYSSTARHS-ARGADGTAELTTTAATRFMKDLHFTGLNG
             310       320       330          340       350

370       380       390       400       410       420
     VGEIGRGIALTLFNLADTLLGGLPTELISSAGGQLFYSRPVVSANGEPTVKLYTSVENAQ
     :::.:::::::::.::::::::::::::::::::::::::::::::::::::::::::::
     VGEVGRGIALTLLNLADTLLGGLPTELISSAGGQLFYSRPVVSANGEPTVKLYTSVENAQ
        360       370       380       390       400       410

430       440       450       460       470       480
     QDKGIAIPHDIDLGESRVVIQDYDNQHEQDRPTPSPAPSRPFSVLRANDVLWLSLTAAEY
     :::::.::::::::::.:::::::::::::::::::::::::::::::::::::::::::
     QDKGVAIPHDIDLGDSRVVIQDYDNQHEQDRPTPSPAPSRPFSVLRANDVLWLSLTAAEY
        420       430       440       450       460       470
```

Fig. 9A

```
            490       500       510       520       530       540
      DQSTYGSSTGPVYVSDSVTLVNVATGAQAVARSLDWTKVTLDGRPLSTIQQYSKTFFVLP
      ::::::::::::::.:::::::::::::::::::::::.:::::::::.:.:::::::::
      DQSTYGSSTGPVYISDSVTLVNVATGAQAVARSLDWSKVTLDGRPLPTVEQYSKTFFVLP
       480       490       500       510       520       530

550       560       570       580       590       600
      LRGKLSFWEAGTTKAGYPYNYNTTASDQLLVENAAGHRVAISTYTTSLGAGPVSISAVAV
      :::::::::::::::::::::::::::::.:.:::::::::::::::.:::::.:::.::
      LRGKLSFWEAGTTKAGYPYNYNTTASDQILIENAAGHRVAISTYTTRLGAGPVAISAAAV
       540       550       560       570       580       590

<--SG3
                  ↓406.3-2-->                           <--406.3-2
           610    ↓    620       630       640       650    <--C2  ↓
      LAPHSALALLEDTLDYPARAHTFDDFCPECRPLGLQGCAFQSTVAELQRLKMKVGKTRELZ
      :::.::::::::::.:::: :::::::::::::::.::::::::::::::::.:::::::
      LAPRSALALLEDTFDYPGRAHTFDDFCPECRALGLQGCAFQSTVAELQRLKVKVGKTRELZ
       600       610       620       630       640       650
```

Fig. 9B

HEPATITIS E VIRUS VACCINE AND METHOD

This application is a continuation-in-part of co-owned, U.S. application Ser. No. 07/822,335, filed Jan. 17, 1992, now abandoned, which is a continuation-in-part of application Ser. No. 07/505,888, filed Apr. 5, 1990, now abandoned, which is a continuation-in-part of U.S. application Ser. No. 07/420,921, filed Oct. 13, 1989, now abandoned, which is a continuation-in-part of U.S. application Ser. No. 07/367,486, filed Jun. 16, 1989, now abandoned, which is a continuation-in-part of U.S. application Ser. No. 07/336,672, filed Apr. 11, 1989, now abandoned, which is a continuation-in-part of U.S. application Ser. No 07/208,997, filed Jun. 17, 1988, now abandoned, all of which are herein incorporated by reference.

FIELD OF THE INVENTION

This invention relates to antigen and antibody vaccine compositions related to enterically transmitted nonA/nonB hepatitis viral agent, also referred to herein as hepatitis E virus (HEV), and to vaccine methods.

References

Arankalle, V. A., et al., *The Lancet*, 550 (Mar. 12, 1988).
Bradley, D. W., et al., *J Gen. Virol.*, 69:1 (1988).
Bradley, D. W. et al., *Proc. Nat. Acad. Sci., USA*, 84:6277 (1987).
Dieckmann, C. L., et al., J. Biol. Chem. 260:1513 (1985).
Engleman, E. G., et al., eds., *Human Hybridomas and Monoclonal Antibodies*, Plenum Press, 1985.
Gravelle, C. R. et al., *J. Infect. Diseases*, 131:167 (1975).
Kane, M. A., et al., *JAMA*, 252:3140 (1984).
Khuroo, M. S., *Am. J. Med.*, 48:818 (1980).
Khuroo, M. S., et al., *Am. J. Med.*, 68:818 (1983).
Lanford, R. E., et al., *In Vitro Cellular and Devel Biol*, 25 (2):174 (1989).
Larrick, J. W. and Fry, K., *Huam Antibod Hybrid*, 2:172 (1991).
Maniatis, T., et al. *Molecular Cloning: A Laboratory Manual*, Cold Spring Harbor Laboratory (1982).
Saiki, R. K., et al., *Science*, 239:487 (1988).
Seto, B., et al., *Lancet*, 11:941 (1984).
Sreenivasan, M. A., et al., *J. Gen. Virol.*, 65:1005 (1984).
Tabor, E., et al., *J. Infect. Dis.*, 140:789 (1979).
Tam, A., et al., Virology, 185:120 (1991).
Yarbough, P. O., J. Virology, 65(11):5790 (1991).
Zola, H., *Monoclonal Antibodies: A Manual of Techniques*, CRC Press, Boca Raton, La., 1987.

BACKGROUND OF THE INVENTION

Enterically transmitted non-A/non-B hepatitis viral agent (ET-NANB, also referred to herein as hepatitis E virus or HEV) is the reported cause of hepatitis in several epidemics and sporadic cases in Asia, Africa, Europe, Mexico, and the Indian subcontinent. Infection is caused usually by water contaminated with feces, although the virus may also spread by close physical contact. The virus does not seem to cause chronic infection.

The viral etiology in HEV has been demonstrated by infection of volunteers with pooled fecal isolates; immune electron microscopy (IEM) studies have shown virus particles with 27–34 nm diameters in stools from infected individuals. The virus particles reacted with antibodies in serum from infected individuals from geographically distinct regions, suggesting that a single viral agent or class is responsible for the majority of HEV hepatitis seen worldwide. No antibody reaction was seen in serum from individuals infected with parenterally transmitted NANB virus (also known as hepatitis C virus or HCV), indicating a different specificity between the two NANB types.

In addition to serological differences, the two types of NANB infection show distinct clinical differences. HEV is characteristically an acute infection, often associated with fever and arthralgia, and with portal inflammation and associated bile stasis in liver biopsy specimens (Arankalle). Symptoms are usually resolved within six weeks. HCV, by contrast, produces a chronic infection in about 50% of the cases. Fever and arthralgia are rarely seen, and inflammation has a predominantly parenchymal distribution (Khuroo, 1980).

The course of HEV is generally uneventful in healthy individuals, and the vast majority of those infected recover without the chronic sequelae seen with HCV. One peculiar epidemiologic feature of this disease, however, is the markedly high mortality observed in pregnant women; this is reported in numerous studies to be on the order of 10–20%. This finding has been seen in a number of epidemiologic studies but at present remains unexplained. Whether this reflects viral pathogenicity, the lethal consequence of the interaction of virus and immune suppressed (pregnant) host, or a reflection of the debilitated prenatal health of a susceptible malnourished population remains to be clarified.

The two viral agents can also be distinguished on the basis of primate host susceptibility. HEV, but not HCV, can be transmitted to cynomolgus monkeys. HCV is more readily transmitted to chimpanzees than is HEV (Bradley, 1987).

In the earlier-filed parent applications, HEV clones, and the sequence of the entire HEV genome sequence were disclosed. From HEV clones, recombinant peptides derived from HEV genomic coding region were produced.

SUMMARY OF THE INVENTION

In one aspect, the invention includes a peptide vaccine composition for immunizing an individual against hepatitis E virus (HEV). The composition includes a pharmacologically acceptable carrier, and a peptide containing the C-terminal 42 amino acids of the putative capsid protein encoded by the second open reading frame of the HEV genome. The peptide preferably includes the amino acid sequence identified by one of the following sequences:

(i) Sequence ID No. 13
(ii) Sequence ID No. 14,
(iii) internally consistent variations between Sequence ID Nos.13 and 14,
(iv) Sequence ID No. 15
(v) Sequence ID No. 16,
(vi) internally consistent variations between Sequence ID Nos.15 and 16,
(vii) Sequence ID No. 17
(viii) Sequence ID No. 18,
(ix) internally consistent variations between Sequence ID Nos.17 and 18,
(x) Sequence ID No. 19
(xi) Sequence ID No. 20, and
(xii) Internally consistent variations between Sequence ID Nos.19 and 20, and (xiii) Sequence ID No. 21

(xiv) Sequence ID No. 22, and (xv) Internally consistent variations between Sequence ID Nos.21 and 22.

In a related aspect, the invention includes a method of inhibiting infection of an individual by HEV, by administering to the subject, by parenteral injection, such as intramuscular or intravenous injection, the above peptide vaccine composition.

In another aspect, the invention includes an antibody vaccine composition effective in neutralizing hepatitis E virus (HEV) infection, as evidenced by the ability of the composition to block HEV infection of primary human hepatocyte cells in culture.

The antibody composition preferably contains an antibody which is immunoreactive with a peptide containing one of the above (i)–(xv) sequences, and preferably with a peptide corresponding to sequences (i)–(iii), (iv–vi) and (vii–xv). In a related aspect, the invention includes a method for preventing or treating HEV infection in an individual, by administering to the subject, by parenteral injection, the above antibody composition.

These and other objects and features of the invention will become more fully apparent when the following detailed description of the invention is read in conjunction with the accompanying drawings.

BRIEF DESCRIPTION OF THE DRAWINGS

FIG. 1 shows the HEV genome, the arrangement of open reading frames in the genome, and the approximate coding regions for peptides 406.3-2, GS3, and trpE-C2;

FIG. 4 shows Southern blots of PCR-amplified RNA from non-infected human primary hepatocytes (lane 4) and primary hepatocytes infected with HEV for increasing times from 3 hours to 11 days (lanes 5–11);

FIG. 5 shows Southern blots of PCR-amplified RNA from HEV-infected human primary hepatocytes in which the infective virus is preincubated with normal pre-immune rabbit serum (lanes 1 and 3) or rabbit antiserum against the HEV antigen HEV 406.3-2(B) (lane 2) and HEV 406.4-2 (M) (lane 4);

FIG. 6 shows Southern blots of PCR-amplified RNA from HEV-infected human primary hepatocytes preincubated with normal human serum (lane 1) and one of a number of different HEV-positive immune human sera (lanes 2–12);

FIG. 7 shows the nucleotide sequences of the HEV ORF2 and ORF3 for Burma (upper line) and Mexico (lower line) strains of HEV;

FIG. 8 shows the amino acid sequences of the ORF3 peptide for Burma (upper line) and Mexico (lower line) strains of HEV; and FIG. 9 shows the amino acid sequences of the ORF2 protein for the Burma (upper line) and Mexico (lower line) strains of HEV.

DETAILED DESCRIPTION OF THE INVENTION

I. Definitions

Figure 2A:
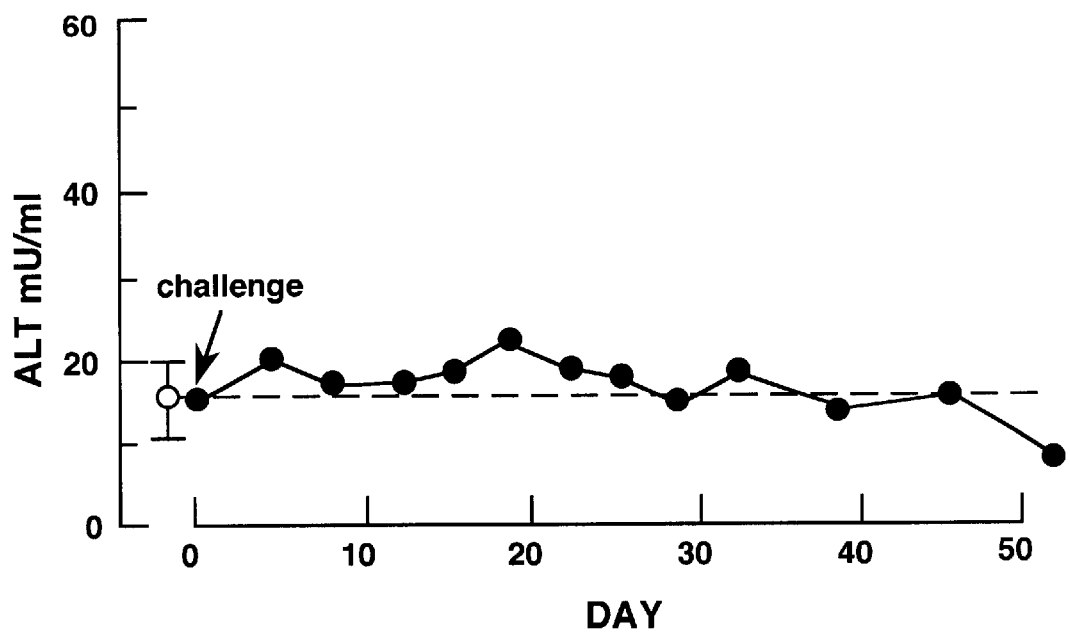
FIGS. 2A and 2B show the blood ALT levels observed after infection of cynomolgus monkeys with a Burma-strain HEV stool sample in animals which were previously immunized with a trpE-C2 HEV antigen (2A) or an alum control (2B)
Figure 2B:
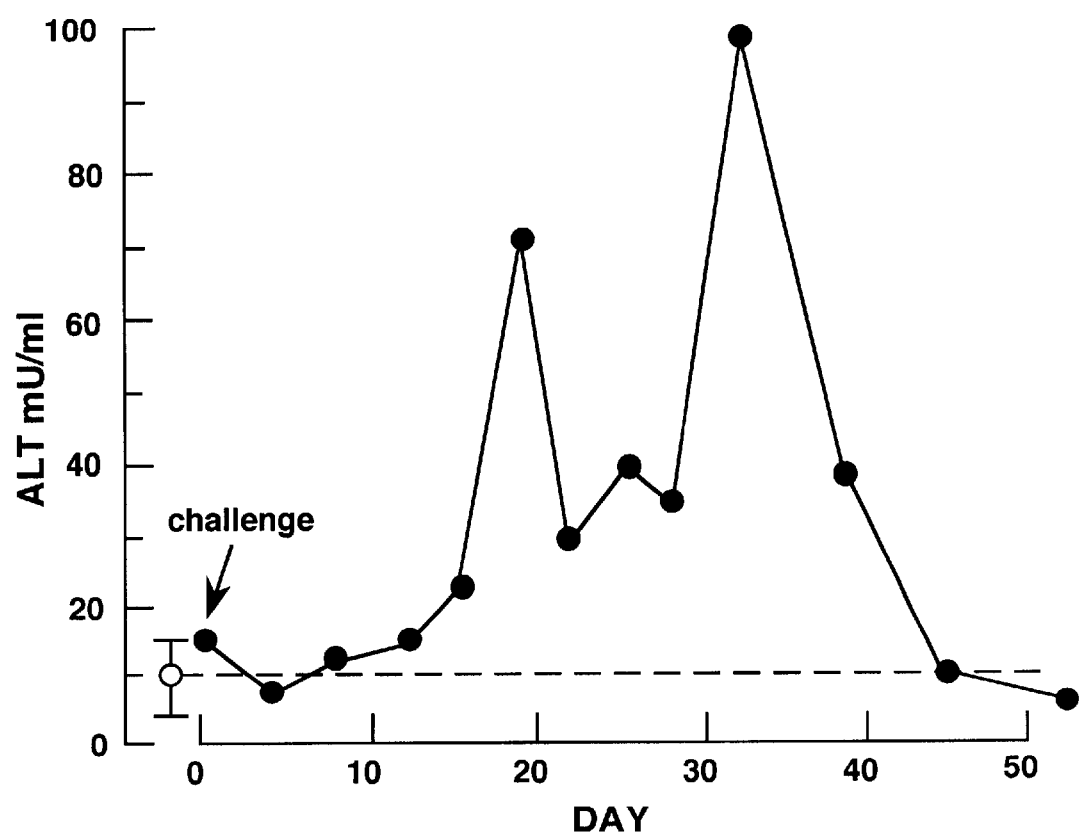
Figure 3A:
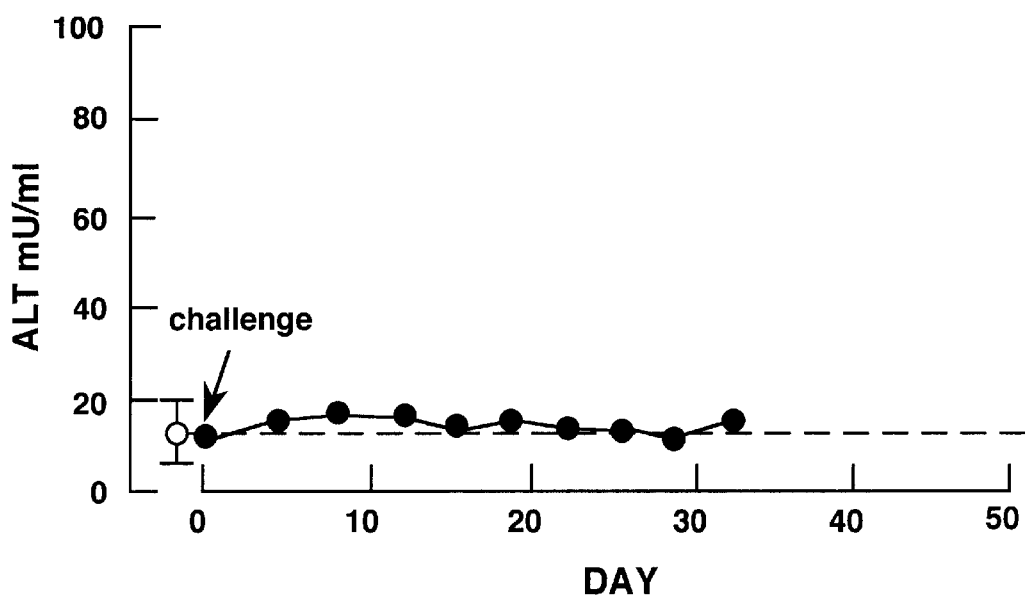
FIGS. 3A and 3B show the blood ALT levels observed after infection of cynomolgus monkeys with a Mexico-strain HEV stool sample in animals which were previously immunized with the trpE-C2 HEV antigen (3A) or an alum control (3B)
Figure 3B:
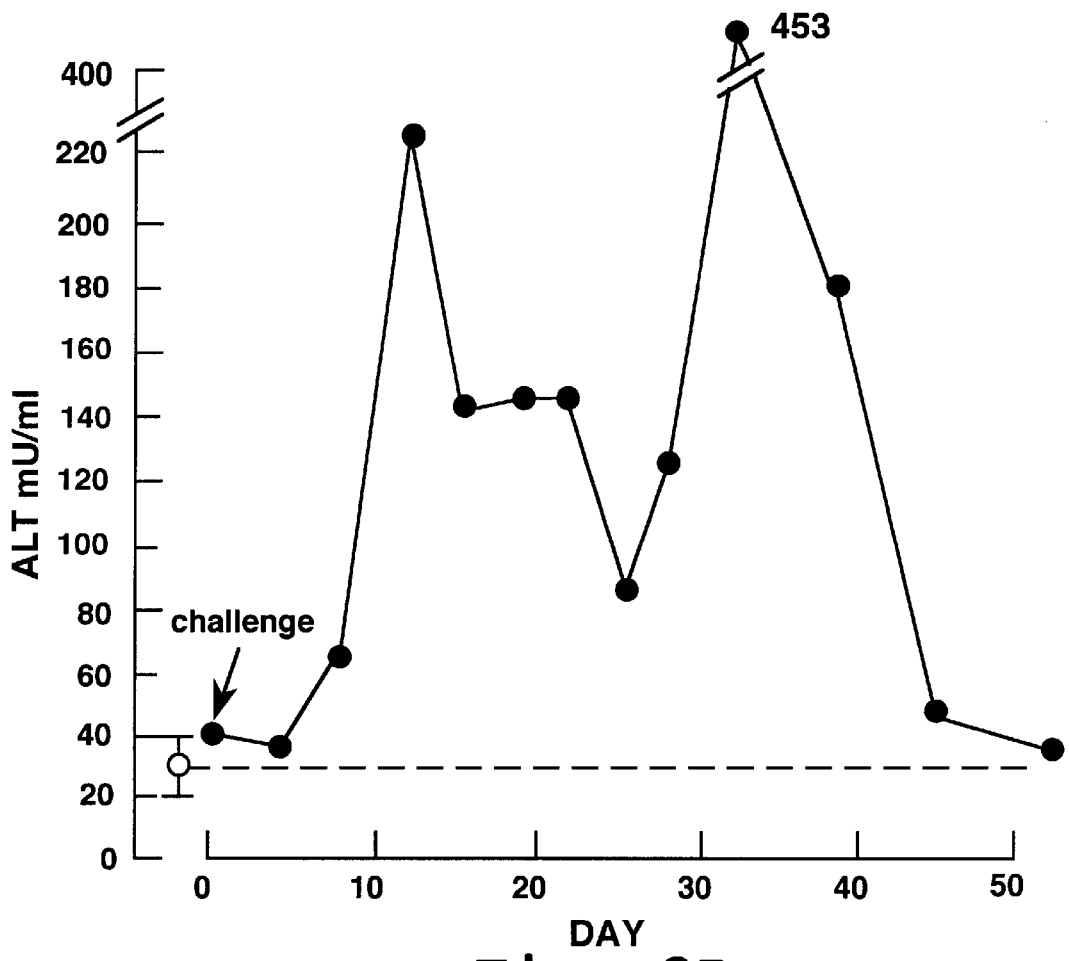

The terms defined below have the following meaning herein:

1. "Enterically transmitted non-A/non-B hepatitis viral agent", "hepatitis E virus", or "HEV" means a virus, virus type, or virus class which (1) causes water-borne, infectious hepatitis, (ii) is transmissible in cynomolgus monkeys, (iii) is serologically distinct from hepatitis A virus (HAV), hepatitis B virus (HBV), hepatitis C virus (HCV), and hepatitis D virus, and (iv) includes a genomic region which is homologous to the 1.33 kb cDNA insert in plasmid pTZKF1 (ET1.1) carried in E. coli strain BB4 identified by ATCC deposit number 67717.

2. Two nucleic acid fragments are "homologous" if they are capable of hybridizing to one another under hybridization conditions described in Maniatis et al., op. cit., pp. 320–323. However, using the following wash conditions: 2×SCC, 0.1% SDS, room temperature twice, 30 minutes each; then 2×SCC, 0.1% SDS, 50° C. once, 30 minutes; then 2×SCC, room temperature twice, 10 minutes each, homologous sequences can be identified that contain at most about 25–30% basepair mismatches. More preferably, homologous nucleic acid strands contain 15–25% basepair mismatches, even more preferably 5–15% basepair mismatches. These degrees of homology can be selected by using more stringent wash conditions for identification of clones from gene libraries (or other sources of genetic material), as is well known in the art.

3. Two amino acid sequences or two nucleotide sequences (in an alternative definition for homology between two nucleotide sequences) are considered homologous (as this term is preferably used in this specification) if they have an alignment score of >5 (in standard deviation units) using the program ALIGN with the mutation gap matrix and a gap penalty of 6 or greater. See Dayhoff, M. O., in *Atlas of Protein Sequence and Structure* (1972) Vol. 5, National Biomedical Research Foundation, pp. 101–110, and Supplement 2 to this volume, pp. 1–10. The two sequences (or parts thereof, preferably at least 30 amino acids in length) are more preferably homologous if their amino acids are greater than or equal to 50% identical when optimally aligned using the ALIGN program mentioned above.

4. A DNA fragment is "derived from" an HEV viral agent if it has the same or substantially the same basepair sequence as a region of the viral agent genome.

5. A protein is "derived from" an HEV viral agent if it is encoded by an open reading frame of a DNA or RNA fragment derived from an ET-NANB viral agent.

6. In two or more known peptide sequences which are more than about 70% homologous in amino acid sequence, a third amino acid sequence will be "internally consistent with the known sequences" if each amino acid in the third sequence is identical to at least one of amino acids in the known sequences.

II. HEV Antigen Vaccine

This section describes methods for preparing and using an HEV antigen vaccine effective, when injected intramuscularly (i.m.), to prevent HEV infection.

A. HEV Genomic Sequences

HEV genomic clones, and sequences corresponding to the entire HEV genome for different HEV strains were obtained according to published methods (Tam, Yarbrough) and as described in the parent applications referenced above. Briefly, RNA isolated from the bile of a cynomolgus monkey having a known HEV infection was cloned, as cDNA fragments, to form a fragment library, and the library was screened by differential hybridization to radiolabeled cDNAs from infected and non-infected bile sources.

The basepair sequence of cloned regions of the HEV fragments in identified clones was determined by standard sequencing methods. With reference to FIG. 1, HEV is a virus with an approximately 7.5 kilobase (kb) single-stranded and polyadenylated RNA genome of positive-sense polarity. Three open reading frames (ORFs) have been assigned to HEV as ORF1, encoding polypeptides with domains of the RNA-directed RNA polymerase and a helicase, ORF2, encoding the putative capsid protein of the virus, and ORF3.

The genomic organization of HEV assigns its non-structural gene(s) at the 5' terminus with the structural gene(s) at the 3' end. Two subgenomic polyadenlated transcripts of approximately 2.0 kb and 3.7 kb in sizes are detected in infected liver and co-terminated at their 3' ends with the 7.5 kb full-length genomic transcript. The genomic organization and expression strategy of HEV suggest that it might be the prototype human pathogen for a new class of RNA virus or perhaps a separate genus within the Caliciviridae family.

The genomic and peptide sequences shown in FIG. 7 correspond to the ORF-2 and ORF-3 regions of Burma (B) (upper lines) and Mexico (M) strains (lower lines) of HEV.

tively. Each peptide includes the carboxyl 324 amino acids of the HEV capsid.

SEQ ID Nos.17 and 18 correspond to the amino acid sequences for the peptides C2(B) and C2(M), respectively. Each includes the carboxyl 461 amino acids of the HEV protein.

SEQ ID Nos.19 and 20 correspond to the amino acid sequences for the entire putative capsid protein encoded by the Burma and Mexico strain ORF2, respectively.

SEQ ID Nos.21 and 22 correspond to the amino acid sequences for the 406.4-2(B) and 406.4-2(M), respectively (FIG. 8). These are 33 amino acid sequences encoded by the ORF3.

Also contemplated are sequences which are internally consistent with the above specified sequences from different strains of HEV antigens. These include Sequence ID No. 13; Sequence ID No. 14, and internally consistent variations between Sequence ID Nos.13 and 14; Sequence ID No. 15; Sequence ID No. 16; and internally consistent variations between Sequence ID Nos.15 and 16; Sequence ID No. 17; Sequence ID No. 18; and internally consistent variations between Sequence ID Nos.17 and 18; Sequence ID No. 19; Sequence ID No. 20; internally consistent variations between Sequence ID Nos.19 and 20; Sequence ID No. 21; Sequence ID No. 22; internally consistent variations between Sequence ID Nos.21 and 22.

For example, the HEV 406.3-2 antigens have the sequence homology shown below for the Burma (B) and Mexico (M) strains. The single dots in the sequence comparison indicate recognized high-probability or "neutral" amino acid substitutions. The blank spaces indicate a non-neutral substitution.

```
                                    10          20          30
MEXICAN(SEQ ID NO.17)
ANQPGHLAPLGETRPSAPPLPPVADLPQPGLRR
::.:.: :::: .:::::::::.:.:::: : ::  BURMA (SEQ ID NO.18)
ANPPDHSAPLGVTRPSAPPLPHVVDLPQLGPRR
                 10          20          30
```

The bases indicated in the middle lines represent conserved nucleotides. The numbering system used in the comparison is based on the Burma sequence. The Burma sequence has SEQ ID No. 1; and the Mexico sequence, SEQ ID No. 2. The region corresponding to ORF2 has SEQ ID nos. 3 and 4 for the Burma and Mexico strains, respectively. The region corresponding to 406.3-2 has SEQ ID Nos.5 and 6 for the Burma and Mexico strains, respectively. The region corresponding to SG3 has SEQ ID Nos. 7 and 8 for the Burma and Mexican strains, respectively. The region corresponding to C2 has SEQ ID Nos. 9 and 10 for the Burma and Mexico strains, respectively. The region corresponding to 406.4-2 has SEQ ID Nos.11 and 12 for the Burma and Mexico strains, respectively.

B. Recombinant Peptide Antigens

The amino acid sequences corresponding to the third and second open reading frames of the Burma and Mexico strains of HEV are given in FIGS. 8 and 9, respectively. The sequence listings shown are as follows:

SEQ ID Nos.13 and 14 correspond to the amino acid sequences for the peptides 406.3-2(B) and 406.3-2(M), respectively. Each peptide is a 42 amino acid peptide in the C-terminal end region of capsid protein encoded by the ORF2, as indicated in the ORF2 sequence (FIG. 9).

SEQ ID Nos.15 and 16 correspond to the amino acid sequences for the peptides SG3 (B) and SG3 (M), respec- A sequence which is internally consistent with these two sequences would have one of the sequences:
AN(Q/P)P(G/D)H(L/S)APLG(E/V)(I/T)RPSAPPLP(P/H)V (A/V)DLPQ (P/L)G(L/P)RR, where X/Y means either amino acid X or amino acid Y.

The ORF3 amino acid sequences, 124 amino acids in length, for the Burma and Mexico strains have an 87.1% identity in the 124 amino acids. The ORF2 amino acid sequences, having 659 amino acids of overlap, have a 93.0 identity in the 659 amino acids.

To prepare the 406.3-2(M) peptide, the lambda gt11 406.3-2 described in Example 3 was subcloned into the glutathione S-transferase vector pGEX to express the 3-2 (M) antigen, as detailed in Example 3, and in the Tam reference.

The 406.3-2(B) antigen can be prepared by PCR amplification of the Burma SEQ ID No. 5 from above by PCR amplification of the PBET1 plasmid (Tam). This plasmid contains a 2.3 kb insert covering the ORF2 and ORF3 for Burma strain HEV sequence. The plasmid is amplified by PCR amplification, using a 5' primer containing an NcoI site and a 3' primer containing a BamHI site (Sakai). The amplified fragment is inserted into the NcoI/BamHI site of a pGEX vector, and expressed in an *E. coli* expression system as described in Example 3.

The SG3(B) peptide was prepared by first amplifying the SEQ ID No. 7 sequence with 5' EcoRI-NcoI and 3' BamHI linkers, using a gt 10 phage BET1 clone plasmid containing the entire ORF2 and ORF3 regions of HEV (B). The amplified fragment was inserted into the EcoRI/BamHI site of a Bluescript™ vector (Stratagene, San Diego, Calif.), according to the manufacturer's instructions. After vector propagation and harvesting, the cloned insert was released by digestion with NcoI and BamHI, and gel purified. The purified fragment was inserted into the NcoI/BamHI site of a PGEX vector, and expressed in an *E. coli* expression system as described in Example 3. The SG3(M) peptide can be prepared similarly, using the SEQ ID No. 8 in place of the SEQ ID No. 7.

The C2(B) peptide is prepared as described in Example 5. Briefly, a gt10 phage BET1 plasmid was digested with EcoRI to release the SEQ ID No. 10 C2 sequence, and this fragment was inserted into a pATH10 trpE fusion vector, and the recombinant fusion protein expressed in an *E. coli* host.

The C2(M) peptide can be prepared, substantially as described above, by PCR amplification of the SEQ ID No. 10, using a 5' primer containing an EcoRI site and a 3' primer containing a BamHI site. The amplified fragment is inserted into the EcoRI/BamHI site of a pGEX vector, and expressed in an *E. coli* expression system as described in Example 3.

The capsid protein (B) was prepared substantially as described above by PCR amplification of the SEQ ID No. 3, from a gt10 BET1 plasmid using a 5' primer containing an NcoI site and a 3' primer containing a BamHI site. The amplified fragment was inserted into the NcoI/BamHI site of a PGEX vector, and expressed in an *E. coli* expression system as described in Example 3. The capsid protein (M) is similarly prepared.

To prepare the 406.4-2(M) peptide, the lambda gt11 406.4-2 described in Example 3 was subcloned into the glutathione S-transferase vector pGEX to express the 3-2 (M) antigen, as detailed in Example 3.

The 406.4-2(B) antigen can be prepared by PCR amplification of the Burma SEQ ID No. 11 from above by PCR amplification, using a 5' primer containing an NcoI site and a 3' primer containing a BamHI site. The amplified fragments is inserted into the NcoI/BamHI site of a pGEX vector, and expressed in an *E. coli* expression system as described in Example 3.

It will be appreciated that other HEV peptides containing selected portions, and preferably C-terminal portions of the HEV capsid protein containing the 406.3-2 sequence, can similarly be prepared, using the HEV genomic-insert plasmids above, with amplification of the desired sequences and cloning into a suitable expression vector, as outlined above, and detailed in Examples 3 and 5.

The coding sequences used in producing the recombinant peptides can be derived from the cloning vectors described above and detailed elsewhere (Tam), or from synthetic nucleotide synthesis using PCR slicing methods to join oligonucleotide fragments, according to known methods, in building up nucleotide sequences.

C. Mature Capsid Protein

HEV peptide antigens may also be obtained from purified HEV virus propagated in primary hepatocytes obtained from primate liver, preferably from human or cynomolgus monkey liver. Methods for preparing primary primate hepatocytes for culture, and culture medium conditions effective to preserve liver-specific functions for extended periods in culture are detailed for human hepatocytes in Example 1 below.

After 3 days of growth in culture, the cells are infected with a pooled inoculum of HEV-infected cynomolgus monkey stool pool (fourth passage), as detailed in Example 2. The presence and level of propagating HEV virus in the cells can be measured by indirect immunofluorescence. Where, for example, the primary cells are cynomolgus cells, the cells can be immunoreacted with human HEV anti-sera, followed by immunoreaction with rabbit anti-human IgG antibodies.

Alternatively, the HEV virus can be detected and measured by selective amplification methods involving initial cDNA formation, and PCR amplification of HEV cDNA sequences by PCR amplification, as detailed in Example 2.

Virus particles can be isolated from HEV infected human hepatocytes in culture medium by pelleting the virus through a 30% sucrose cushion by ultracentrifugation. The pelleted virus may be further purified, if desired, by zonal centrifugation through a 10–40% sucrose gradient, combining peak virus fractions.

Other methods for separating virus particles from soluble culture-medium components may be used. For example, clarified culture medium can be passed through a size-exclusion matrix, to separate soluble components by size exclusion.

Alternatively, the clarified culture medium can be passed through an ultrafiltration membrane having a 10–20 nm pore size capable of retaining virus particles, but passing solute (non-particulate) culture medium components.

The present invention allows glycosylation and other post-translation modifications in intact HEV capsid protein. Capsid isolation from the viral particles can be carried out by standard methods, such as ion exchange and size-exclusion chromatography, and HPLC purification, after solubilization of the virus particles in a solubilizing medium, such as a solution of a non-ionic surfactant. The protein may be purified by affinity chromatography, employing, for example, antibodies purified from anti-HEV antisera.

D. Preparation of Vaccine Compositions

The recombinant or intact HEV capsid or capsid fragment peptides (HEV capsid antigens) described above are incorporated into a vaccine composition, according to known procedures, to enhance the antigenicity of the injected antigens.

In one composition, the HEV antigen is covalently coupled to a carrier protein, such as keyhole limpet hemocyanin, and injected either in solution form or in combination with an adjuvant. Alternatively, where the HEV antigen is prepared as part of a fusion protein, the non-HEV moiety of the protein may serve as the carrier protein. The derivatized or fusion protein is carried in a pharmaceutically acceptable carrier, such as in solution or in an adjuvant, such as converted alum.

Alternatively, the free peptide itself, e.g., the HEV C2 peptide, may be formulated in alum or used without adjuvant. A suitable adjuvanted vaccine has a preferred antigen concentration of about 1 mg peptide antigen/mg alum, and not to exceed 80 mg of alum per injection.

III. Antigen Vaccine Method

In a related aspect, the invention is directed to a method of inhibiting infection of an individual by hepatitis E virus, by administering to the subject, by parenteral injection, e.g., intramuscular or intravenous injection, the vaccine composition of the invention.

Preferred vaccine compositions, for use in the method are those in which the HEV antigen includes the sequence in the peptides identified by:

Sequence ID No. 13; Sequence ID No. 14, and internally consistent variations between Sequence ID Nos.13 and 14; Sequence ID No. 15; Sequence ID No. 16; and internally consistent variations between Sequence ID Nos.15 and 16;

Sequence ID No. 17; Sequence ID No. 18; and internally consistent variations between Sequence ID Nos.17 and 18; Sequence ID No. 19; Sequence ID No. 20; internally consistent variations between Sequence ID Nos.19 and 20; Sequence ID No. 21; Sequence ID No. 22; internally consistent variations between Sequence ID Nos.21 and 22.

The antigen vaccine composition is preferably administered intramuscularly in a series of inoculations, for example, two-three injections given at four week intervals.

In the method detailed in Example 7, cynomolgus monkeys were injected i.m. with the C2 fusion protein trpE-C2 (B), formulated in a converted alum adjuvant or with no adjuvant. Four animals received the alum plus trpE-C2(B) antigen in two injections, spaced one month apart. Two other animals received alum only on the same vaccination schedule. None of the animals showed the presence of any anti-HEV serum antibody 4 weeks after the second injection, as judged by Western blotting using a fusionless C2 HEV antigen or by a separate fluorescence antibody blocking assay.

At this stage, two of the four experimental animals received a third inoculation of non-adjuvanted, insoluble trpE-C2 peptide antigen. Four weeks later, these animals showed anti-HEV antibodies, as evidenced by Western blots. These results suggest that the trpE-C2 antigen may be more effective when administered in the absence of alum, possibly because of alum-denaturation of the antigen during the alum co-precipitation procedure.

One month after the final inoculation, the animals were challenged with an intravenous injection of a third-passage human stool previously shown to be highly infectious for HEV (Burma strain) or with a Mexico-strain human HEV stool sample. At selected intervals after inoculation, serum samples from the animals were used to measure ALT (alanine transferase) levels, as an indication of necrosis and hepatocellular degradation. Liver biopsy samples were also assayed for the presence of HEV antigens by a direct fluorescent antibody assay (FA).

FIG. 2A shows the change in liver ALT levels in the period following infection with Burma-strain HEV virus, in one of the animals which received a third dose of trpE-C2. As seen, there was no evidence of elevated ALT levels in the 7 and ½ week period following infection. The liver biopsy samples also showed no evidence of HEV antigen.

FIG. 2B shows ALT levels measured after HEV (B) infection of a control animal (alum alone injections) which was infected intravenously with the Burma strain HEV. The elevated ALT levels indicate the level of infection which is expected in the absence of vaccine protection. HEV antigen was also detected in the liver biopsy samples. A similar result was observed in the animal which received two injections of trpE-C2 alum composition, but not the third alum-free vaccination, as described above.

FIG. 3A shows the change in liver ALT levels following infection with Mexico-strain HEV virus, in one of the animals which received a third dose of trpE-C2. Again, there was no evidence of elevated ALT levels out to day 32(The animal died of unrelated causes at day 32). The liver biopsy samples also showed minimal evidence of HEV antigen. This result demonstrates that an antigen vaccine directed against one HEV strain can provide protective immunity against other HEV strains.

FIG. 3B shows ALT levels measured after HEV infection of a control animal (alum alone injections) which was infected intravenously with the Mexico strain of HEV. High levels of infection (ALT activity) were observed. A similar result was observed in the animal which received two injections of trpE-C2 alum composition, but not the third alum-free vaccination, as described above.

Details of the vaccination method just reported are given in Example 5.

IV. Vaccine Composition

In another aspect, the invention includes an antibody vaccine composition effective in neutralizing HEV infection, as evidenced by the ability of the composition to block HEV infection in HEV-infectable primary hepatocytes in culture. Two exemplary primary cells are human and cynomolgus monkey cells.

The antibodies in the composition are preferably immunoreactive with a peptide containing one of the sequences: Sequence ID No. 13; Sequence ID No. 14, and internally consistent variations between Sequence ID Nos. 13 and 14. As will be seen below, antibodies prepared against the 406.3-2 antigen (M) are effective to block HEV infection in human primary hepatocytes.

Antibodies which are immunoreactive with larger capsid peptides or proteins containing the carboxy terminal of SEQ ID No. 13 or 14 are also preferred. These may include, specifically Sequence ID No. 15; Sequence ID No. 16; and internally consistent variations between Sequence ID Nos.15 and 16. As will be seen below, human sera which are effective to prevent HEV infection of human primary hepatocyes are immunoreactive with the SG3 peptides defined by these sequences.

Antibodies which are immunoreactive with the trpE-C2 peptides defined by Sequence ID No. 17; Sequence ID No. 18; and internally consistent variations between Sequence ID Nos.17 and 18 are also preferred, as are antibodies immunoreactive with the entire capsid protein, as defined by Sequence ID No. 19; Sequence ID No. 20; internally consistent variations between Sequence ID Nos.19 and 20; and antibodies that are immunoreactive with the product of ORF3, as defined in part by Sequence ID No. 21; Sequence ID No. 22; and internally consistent variations between Sequence ID Nos 21 and 22.

The antibodies may be obtained as polyclonal antibodies from antisera, prepared for example, by immunization of a suitable animal, such as a rabbit or goat, with one of the HEV antigens specified above. Alternatively, polyclonal antibodies may be obtained from human or other primate HEV antisera. Anti-HEV polyclonal antibodies from the antisera may be purified or partially purified according to standard methods, such as used to obtain partially purified serum IgG fractions (see, e.g., *Antibodies: A laboratory Manual,* 1988, Cold Springs Harbor Lab). Alternatively anti-HEV antibodies can be obtained in purified form by affinity chromatography, employing a solid support derivatized with one of the capsid antigens described above.

In another embodiment, the antibodies are monoclonal antibodies secreted by hybridoma cell lines. To prepare the hybridoma cell lines, lymphocytes from an immunized animal, preferably mouse or human, are immortalized with a suitable immortalizing fusion partner, according to established methods (e.g., Engleman, Zola).

Alternatively, human monoclonal antibodies may be produced by recombinant methods, in which light and heavy human anti-HEV IgG genes obtained from cultured lymphocytes are inserted into suitable expression vectors, and used to co-infect a suitable host. Methods for obtaining and cloning light and heavy genes from human lymphocytes, and for expressing the cloned genes in a co-infected host cell are known (larrick).

The anti-HEV antibodies are formulated in a suitable solution for injection, typically by intramuscular, subcutaneous or intravenous route, to form the vaccine composition.

B. Neutralizing Activity of Anti-406.3-2 Antibodies To demonstrate the neutralizing capability of antibodies prepared as above, antibodies against the 406.3-2(B) antigen were tested for their abilities to block HEV infection in human primary hepatocytes in culture.

The primary hepatocytes were prepared and cultured according to published procedures and as detailed in Example 1. The unique culture conditions allow for long-term cell growth in culture without loss of specialized hepatocyte function, as evidenced by the cells' continued ability to make and secrete liver-specific proteins, such as serum albumin, up to several months after initial culturing, as described in Example 1.

The cultured cells were inoculated with either normal human sera or a cynomolgus stool preparation. To demonstrate HEV infection in the cells, the cells were examined on days 1–11 after infection for the presence of HEV RNA, using a combination of reverse transcriptase, to form cDNA's, and polymerase chain reaction (PCR) to amplify HEV-specific cDNA. The amplified fragment is expected to have a 551 basepair length. FIG. 4 shows Southern blots of the amplified material, using an HEV ORF2 radiolabeled probe for detecting amplified HEV sequence.

The results are shown in FIG. 4. Lanes 1–3 are controls. Lane 4 is total amplified material from cells inoculated with normal (non-infected) sera. Lanes 5–11 show amplified material 3 hours, 1 day, 3 days, 5 days, 7 days, 9 days, and 11 days after infection with the cyno stool sample, respectively. The results show that HEV propagated in human primary hepatocytes within one day after initial infection (lane 6). There was a time-dependent increase at the level of HEV replication up to 5 days post infection (lanes 7 and 8), which appeared to decrease thereafter (lanes 9–11). There was no evidence of HEV in total cellular RNA isolated from uninfected primary cells.

Rabbit antisera against antigen peptides 406.3-2(B) and 406.4-2(M) and 406.4-2(B) were prepared. As noted above, the 406.3-2 peptide is from the carboxy terminal end region of the HEV capsid protein, and the 406.4-2 peptide, from the peptide encoded by the HEV ORF3. Preimmune rabbit serum or rabbit antiserum against one of HEV antigens was added to the cyno stool inoculum, at a 1:20 dilution, and the antibody was incubated with the viral preparation. The antibody-treated stool sample was then used to infect human primary hepatocytes. 14 days later, the cells were examined for HEV infection by the RT/PCR/Southern blot method just described, except employing primers which are expected to yield a 448 basepair amplified fragment.

The results are shown in FIG. 5. Lanes 1 and 3 in this figure show amplified RNA from cells infected with cyno stool sample previously incubated with human preimmune serum. The 448 basepair band in the figure indicates HEV infection. The second lane corresponds to cells which were exposed to anti-406.3-2(B) rabbit antisera, and indicates virtually complete absence of HEV infection. Lane 4 shows amplified material from cells exposed to anti-406.4-2(M) rabbit antisera. The antibody showed little or no protective effect against HEV infection. However, as shown in Example 5, both anti-406.3-2(B) and anti-406.4-2(B) were shown to offer protective effect against HEV infection.

C. Neutralizing Activity of Anti-406.4-2(B) Antibody

D. Neutralizing HEV Antisera

Another source of neutralizing antibodies, in accordance with the invention, is human HEV antisera which is characterized by immunospecific reaction to the 406.3-2 antigen and the SG3 antigen, both described above.

To examine the neutralizing antibody characteristics of human HEV antisera, a panel of human antisera were tested for the ability to block HEV infection of cultured hepatocytes, substantially as described above. The ten HEV positive human antisera are shown in Table 1 below, and are from patients who developed HEV infection in India, Pakistan, and Mexico. The antisera were not tested for strain type.

Briefly, cultured cells were exposed to HEV-positive cyno stool treated with samel (Burma strain) treated with normal pooled serum or HEV antiserum, and tested for the presence of HEV-specific nucleic acid sequences, by PCR amplification and Southern blotting with an HEV radiolabled probe. The Southern blots are shown in FIG. 6. The lane numbers of the 12 serum samples are given in parentheses in Table 1 below. As seen from FIG. 6, and indicated in Table 1, the antisera which were effective in neutralizing HEV were India 10 (lane 2), India 18 (lane 3), India 210 (lane 5), India 265 (lane 8), Pak 143 (lane 9), and Pak 336 (lane 10). Other human sera, however, showed very little (lane 11, Mex 387C) or no effect (lane 4, India 29; lane 6, India 242; lane 7, India 259; lane 12, Mex 387C[IgG]) in their ability to neutralize HEV infection. As a negative control, the normal human serum pool revealed absolutely no neutralizing activity against HEV (lane 1).

TABLE 1

| Serum | Clinical | Neutralizing Activity |
|---|---|---|
| normal (1) | pooled | – |
| India 10 (2) | — | + |
| India 18 (3) | acute, import | + |
| India 29 (4) | acute, import | – |
| India 210 (5) | acute | + |
| India 242 (6) | acute, fulminant | – |
| India 259 (7) | acute, fulminant | – |
| India 265 (8) | acute | + |
| Pak 143 (9) | acute | + |
| Pak 336 (10) | acute | + |
| Mexico F387c (11) | convalescent | – |
| Mexico F387c (IgG) (12) | convalescent | – |

Several of the human antisera were tested for their IgG and IgM immunoreactivity to 406.3-2(M), 406.4-2(M) and 406.4-2(B) antigens noted above. Reaction with IgM antibodies tends to indicate early-phase infection, whereas immunoreactivity with IgG is indicative of both early and later stages of infection. Reaction was measured in an ELISA test. The results are shown in Table 2A and 2B, where a "+" sign indicates a positive reaction; numbers in the table indicate dilution titre of IgG against the specific recombinant protein indicated.

TABLE 1A

| Serum Samples | IgG | | | Neutralizing Activity | Clinical |
|---|---|---|---|---|---|
| | 406.3–2 (M) | 406.4–2 (B) | 406.4–2 (M) | | |
| Normal Human | – | – | – | – | Pooled Human Serum |
| India 18 | + | + | + | + | acute, import |

TABLE 1A-continued

| Serum | IgG | | | Neutralizing | |
|---|---|---|---|---|---|
| Samples | 406.3–2 (M) | 406.4–2 (B) | 406.4–2 (M) | Activity | Clinical |
| India 29 | – | + | – | – | acute, import |
| India 210 | + | + | + | + | acute |
| India 242 | + | + | + | – | acute, fulminant |
| India 259 | + (500) | + (>5000) | + (2000) | – | acute, fulminant |
| India 265 | + (>5000) | + (>5000) | + (1000) | + | acute |

TABLE 1B

| Serum | IgM | | |
|---|---|---|---|
| Samples | 406.3–2 (M) | 406.4–2 (B) | 406.4–2 (M) |
| Normal Human | ND | ND | ND |
| India 18 | – | – | – |
| India 29 | – | – | – |
| India 210 | – | – | – |
| India 242 | + | + | – |
| India 259 | + | + | – |
| India 265 | + | + | – |

The data from the table indicates that those human antisera capable of neutralizing were positive by an IgG ELISA for antibodies to the HEV 3-2(M) epitope. India 29 was not positive for IgG(s) to HEV 3-2(M) and did not neutralize HEV infection (lane 4). Although India 242 and India 259 were positive for IgG(s) to HEV 406.3-2(M), they were also positive for IgM to HEV 406.3-2(M), which is indicative of an early stage, HEV infection. Therefore in these particular samples, the levels of IgG(s) to HEV 3-2(M) elicited might be sufficient to neutralize HEV infection of primary human hepatocytes.

To further study the correlation of neutralizing activities of sera of HEV-infected humans with immunoreactivities to HEV3-2 epitope, Western blotting analyses were performed on these human serum samples, with the results shown in Table 3. As seen in this table, India 18, India 265, and especially India 210, previously shown to be neutralizing for HEV infection, were immunoreactive to HEV406.3-2(M) in these Western blotting analyses and their immunoreactivities correlated with their neutralizing activities.

As a confirmation for the specific immunoreactivities of these sera to HEV406.3-2(M), Western analyses were performed against the fusion protein SG3 (B), which contains the 329 carboxy-terminal amino acids (nucleotides 6146–7129) of ORF-2 of HEV Burma strain. The immunoreactivities of these sera against HEV406.3-2(M) and SG3 [or HEV406.3-2(B)] were perfectly matched (Table 3).

TABLE 3

| Serum Samples | 406.3–2 (M) ELISA Titre | 406.3–2 (M) Western Blot | SG3 Western Blot | Neutralizing Activity |
|---|---|---|---|---|
| Normal Human | — | – | – | – |
| India 18 | 2000 | ++ | + | + |
| India 29 | — | – | – | – |
| India 210 | 100 | ++ | + | + |
| India 242 | 500 | – | – | – |

TABLE 3-continued

| Serum Samples | 406.3–2 (M) ELISA Titre | 406.3–2 (M) Western Blot | SG3 Western Blot | Neutralizing Activity |
|---|---|---|---|---|
| India 259 | 500 | ± | – | – |
| India 265 | 5000 | +++ | +++ | + |

Thus, human HEV antisera which provide a suitable source of neutralizing antibodies are those characterized by (a) immunoreactivity with a 406.3-2 antigen, and (b) the SG3 antigen, both as evidenced by immunoreactivity in a Western blot, i.e., where the antigen is in an exposed, accessible configuration.

More generally, a preferred vaccine composition of the invention contains antibodies immunospecific against the 406.3-2 antigenic and against the SG3 antigenic peptide. The vaccine composition includes the immunospecific antibodies in a suitable carrier for parenteral injection.

The antibody vaccine composition is used, according to another aspect of the invention, for preventing or treating HEV infection in humans.

The following examples, which illustrate various methods and compositions in the invention, are intended to illustrate, but not limit the scope of the invention.

Materials

Enzymes: DNAse I and alkaline phosphatase were obtained from Boehringer Mannheim Biochemicals (BMB, Indianapolis, IN); EcoRI, EcoRI methylase, DNA ligase, and DNA Polymerase I, from New England Biolabs (NEB, Beverly Mass,); and RNase A was obtained from Sigma (St. Louis, Mo.).

Other reagents: EcoRI linkers were obtained from NEB; and nitro blue tetrazolium (NBT), S-bromo-4-chloro-3-indolyl phosphate (BCIP) S-bromo-4-chloro-3-indolyl-B-D-galactopyranoside (Xgal) and isopropyl B-D-thiogalactopyranoside (IPTG) were obtained from Sigma. cDNA synthesis kit and random priming labeling kits are available from Boehringer-Mannheim Biochemical (BMB, Indianapolis, Ind.).

EXAMPLE 1

Human Primary Hepatocytes in Culture

A. Isolation of hepatocytes.

Hepatocytes were isolated from human liver obtained from Stanford University Medical Center. The liver was either perfused in situ or excised as a wedge for perfusion in laboratory. The initial perfusion was performed for 10 minutes at 60 ml/min using $Ca^{++}$-, $Mg^{++}$-free Hanks' balanced salt solution supplemented with 10 mM HEPES (pH7.4) and 0.5 mM [ethylene bis(oxyethylenenitrillo]-tetraacetic acid. Perfusion was continued for additional 20 minutes using Williams' medium E (WME) supplemented with 10 Mm HEPES (pH7.4) and 100 U/ml collagenase (type I, Sigma Chemical Co., St. Louis, Mo.).

After perfusion the liver capsule was removed using fine forceps, and hepatocytes were dislodged by gentle shaking in collagenase solution. The hepatocyte suspension was filtered through several layers of gauze and mixed with an equal volume of WMW containing 10% fetal bovine serum (FBS). Hepatocytes were sedimented by centrifugation at 50 ×g for 5 minutes and resuspended in WME containing 5% FBS. Hepatocytes were sedimented and resuspended in the manner for 2 additional times. The final cell preparation was further filtered through several layers of gauze before examining for viability using trypan blue. The cells were plated at a density of 2×10 cells per 60-mm Primaria plates (Falcon) pre-coated with collagen (Collaborative Research).

Cultures were incubated at 37° C. in 5% $CO_2$ for 3 hours to allow attachment and the medium was changed to a serum-free formulation and every 48 hrs thereafter. The serum-free formulation was a WME-based medium supplemented with growth factors, hormones, 10 mM HEPES (pH7.4), 100 ug/ml gentamycin, as has been described (Lanford).

B. Detection of Liver-Specific Proteins.

Human hepatocyte cultures were maintained in serum-free medium for various period of time and labeled with [$^{35}$S]-methionine for 24 hrs. The medium was adjusted to contain 1 mM PMSF, 1 mM EDTA, and 1% "NONIDET P-40" detergent ("NP-40"—an octylphenol-ethylene oxide condensate containing an average of 9 moles ethylene oxide per mole of phenol) Antibodies specific for the different plasma proteins were bound to protein A-agarose beads, the beads were washed with PBS, and aliquots of the labeled medium were incubated for 16 hrs at 4° C. with the antibody-bead complexes. The beads were washed 3 times with a buffer containing 1% NP40, and immunoprecipitated proteins were eluted with gel electrophoresis sample buffer containing 2% SDS and 2% 2-mercaptoethanol. Samples were analyzed by gradient SDS-PAGE (4 to 15%) and autoradiography.

EXAMPLE 2

In Vitro HEV Infection of Primary human Hepatocytes

A. HEV Infection of human hepatocytes.

The HEV-infected cynomolgus monkey #73 stool pool (fourth passage) was used as an inoculum for infections of primary human hepatocytes. Various amounts of inoculum was diluted in 1 ml of serum-free medium (SFM) and applied to the culture during a 3 hr incubation period. This solution was then supplemented with 2 ml of fresh SFM and the entire mixture was incubated overnight. The next day, cell monolayers were washed with WME (10 mM HEPES, pH7.4) for three times and changed to fresh SFM, which was changed at two day intervals thereafter.

B. Immunofluorescence staining assay.

Primary cynomolgus monkey hepatocytes were isolated and plated in tissue culture plates with collagen-coated coverslips as described. Cells on coverslips were infected with either the HEV-infected cynomolgus monkey #73 stool pool or the NIH normal human serum three days after initial plating. The infections were allowed to proceed for 2 weeks. Cells on coverslips were fixed in 90% acetone at room temperature for 1 minute. The coverslips were then air-dried.

The coverslips were blocked in 1% goat serum in PBS for 1 hour, washed with PBS for three times, and incubated with a mixture of rabbit antisera against HEV recombinant proteins 1L6, 4-2, and 6-1-4 at room temperature for 3 hours. The coverslips were again washed with PBS for 3 times and reacted with fluorescein isothiocyanate-conjugated (FITC) goat anti-rabbit IgG(H+L) (Zymed) diluted in PBS-1% goat serum for 30 minutes. After the coverslips were washed with PBS for 3 times and air-dried, they were mounted with FITC glycerol solution and examined under a fluorescent microscope.

C. Reverse transcription/polymerase chain reaction (RT/PCR).

HEV infection of primary cynomolgus macaque hepatocytes was evaluated by RT/PCR assays. The primers for cDNA synthesis and PCR were based on the nucleotide sequences of the full-length HEV cDNA (A. Tam et al.). Primers HEV3.2SF1 (nt 6578–6597) and HEV3.2SF2(nt 6650–6668) are of sense polarity from the ORF2 region of the viral genome and HEV3.2SR1 (nt 7108–7127) and HEV3.2SR2 (nt 7078–7097) are antisense primers within the region.

Following extraction of total cellular RNA from HEV-infected cells using one-step guanidinium procedure or HEV-infected supernatants according to the method of Sherker et al., aliquots of RNA samples were heat-denatured at 95° C. for 5 minutes and subjected to reverse transcription at room temperature for 5 minutes and 42° C. for 60 minutes using 200 units per reaction of MMLV-reverse transcriptase (BRL) in a 20 ul reaction volume containing 20 units of RNasin (Promega), 1×PCR buffer (Perkin-Elmer Cetus), with a concentration of 1 mM each deoxyribonucleotide (Perkin-Elmer Cetus), and 2.5 uM of HEV3.2SR1 primer. The reaction mixture was then heat-treated at 95° C. for 5 minutes to denature the MMLV-reverse transcriptase.

Ten microliters of the cDNA synthesis product was used for PCR in a final volume of 50 ul with 0.5 uM HEV3.2SF1 primer, 1.25 units Taq DNA polymerase (AmpliTaq, Perkin-Elmer Cetus), and 1×PCR buffer, overlayed with 50 ul of mineral oil, and subjected to 40 cycles of PCR in a Perkin-Elmer thermocycler (95° C.×1 minute; 52° C.×2 minutes; 72° C.×30 seconds). Ten microliters of the first-round PCR product then underwent another 40 cycles of nested PCR (95° C.×1 minute; 55° C.×2 minutes; 72° C.×30 seconds) in a total volume of 50 ul containing the internal PCR primers HEV3.2SF2 and HEV3.2SR2.

First- and second-round PCR products were subjected to agarose electrophoresis, ethidium bromide stained and photographed under UV light. The results are shown in FIG. 4, discussed above. Southern transfer was performed and filters were hybridized with [$^{32}$P-dCTP]-labeled internal probe HEVORF2-7 exclusive of the primers (nt 6782–6997), and autoradiography performed.

EXAMPLE 3

Preparation of 406.3-2 and 406.4-2 AntiqGns

A TZKF1 plasmid (ET1.1), ATCC deposit number 67717, was digested with EcoRI to release the 1.33 kb HEV insert which was purified from the linearized plasmid by gel electrophoresis. The purified fragment was suspended in a standard digest buffer (0.5M Tris HCl, pH 7.5; 1 mg/ml BSA; 10 mM MnC12) to a concentration of about 1 mg/ml and digested with DNAse I at room temperature for about 5 minutes. These reaction conditions were determined from a prior calibration study, in which the incubation time required to produce predominantly 100–300 basepair fragments was determined. The material was extracted with phenol/chloroform before ethanol precipitation.

The fragments in the digest mixture were blunt-ended and ligated with EcoRI linkers. The resultant fragments were analyzed by electrophoresis (5–10V/cm) on 1.2% agarose gel, using PhiX174/HaeIII and lambda/HindIII size markers. The 100–300 bp fraction was eluted onto NA45 strips (Schleicher and Schuell), which were then placed into 1.5 ml microtubes with eluting solution (1 M NaCl, 50 mM arginine, pH 9.0), and incubated at 67° C. for 30–60 minutes. The eluted DNA was phenol/chloroform extracted and then precipitated with two volumes of ethanol. The pellet was resuspended in 20 ml TE (0.01 M Tris HCl, pH 7.5, 0.001 M EDTA).

B. Cloning in an Expression Vector

Lambda gt11 phage vector (Huynh) was obtained from Promega Biotec (Madison, Wis.). This cloning vector has a unique EcoRI cloning site 53 base pairs upstream from the beta-galactosidase translation termination codon. The genomic fragments from above, provided either directly from coding sequences 5) or after amplification of cDNA, were introduced into the EcoRI site by mixing 0.5–1.0 mg EcoRI-cleaved gt11, 0.3–3 ml of the above sized fragments, 0.5 ml 10X ligation buffer (above), 0.5 ml ligase (200 units), and distilled water to 5 ml. The mixture was incubated overnight at 14° C., followed by in vitro packaging, according to standard methods (Maniatis, pp. 256–268).

The packaged phage were used to infect *E. coli* strain KM392, obtained from Dr. Kevin Moore, DNAX (Palo Alto, Calif.). Alternatively, *E. Coli* strain Y1090, available from the American Type Culture Collection (ATCC #37197), could be used. The infected bacteria were plated and the resultant colonies were checked for loss of beta-galactosidase activity-(clear plaques) in the presence of X-gal using a standard X-gal substrate plaque assay method (Maniatis). About 50% of the phage plaques showed loss of beta-galactosidase enzyme activity (recombinants).

C. Screening for HEV Recombinant Proteins

HEV convalescent antiserum was obtained from patients infected during documented HEV outbreaks in Mexico, Borneo, Pakistan, Somalia, and Burma. The sera were immunoreactive with VLPs in stool specimens from each of several other patients with ETNANB hepatitis.

A lawn of *E. coli* KM392 cells infected with about 10⁴ pfu of the phage stock from above was prepared on a 150 mm plate and incubated, inverted, for 5–8 hours at 37° C. The lawn was overlaid with a nitrocellulose sheet, causing transfer of expressed HEV recombinant protein from the plaques to the paper. The plate and filter were indexed for matching corresponding plate and filter positions.

The filter was washed twice in TBST buffer (10 mM Tris, pH 8.0, 150 mM NaCl, 0.05% "TWEEN 20" (a polyoxyethylenesorbitan monolaurate with a fatty acid composition of approximately 55% lauric acid, with a balance composed primarily of myristic, palmitic and steric acids), blocked with AIB (TBST buffer with 1% gelatin), washed again in TBST, and incubated overnight after addition of antiserum (diluted to 1:50 in AIB, 12–15 ml/plate). The sheet was washed twice in TBST and then contacted with enzyme-labeled anti-human antibody to attach the labeled antibody at filter sites containing antigen recognized by the antiserum. After a final washing, the filter was developed in a substrate medium containing 33 ml NBT (50 mg/ml stock solution maintained at 4° C.) mixed with 16 ml BCIP (50 mg/ml stock solution maintained at 4° C.) in 5 ml of alkaline phosphatase buffer (100 mM Tris, 9.5, 100 mM NaCl, 5 mM MgC12). Purple color appeared at points of antigen production, as recognized by the antiserum.

D. Screening Plating

The areas of antigen production determined in the previous step were replated at about 100–200 pfu on an 82 mm plate. The above steps, beginning with a 5–8 hour incubation, through NBT-BCIP development, were repeated in order to plaque purify phage secreting an antigen capable of reacting with the HEV antibody. The identified plaques were picked and eluted in phage buffer (Maniatis, p. 443).

Two subclones which were selected are the 406.3-2 and 406.4-2 clones whose sequences are set forth above. These sequences were isolated from an amplified cDNA library derived from a Mexican stool. Using the techniques described in this section, polypeptides expressed by these clones have been tested for immunoreactivity against a number of different human HEV-positive sera obtained from sources around the world. As shown in Table 4 below, 8 sera immunoreactive with the polypeptide expressed by the 406.4-2, and 6 sera immunoreacted with polypeptide expressed by the 406.3-2 clone.

For comparison, the Table also shows reactivity of the various human sera with the non structural peptide Y2. Only one of the sera reacted with the polypeptide expressed by this clone. No immunoreactivity was seen for normal expression products of the gt11 vector.

TABLE 4

Immunoreactivity of HEV Recombinant Proteins: Human Sera

| Sera | Source | Stage[1] | 406.3-2 | 406.4-2 | Y2 | lgt11 |
|---|---|---|---|---|---|---|
| FVH-21 | Burma | A | – | – | – | – |
| FVH-8 | Burma | A | – | + | + | – |
| SOM-19 | Somalia | A | + | + | – | – |
| SOM-20 | Somalia | A | + | + | – | – |
| IM-35 | Borneo | A | + | + | – | – |
| IM-36 | Borneo | A | – | – | – | – |
| PAK-1 | Pakistan | A | + | + | – | – |
| FFI-4 | Mexico | A | + | + | – | – |
| FFI-125 | Mexico | A | – | + | – | – |
| F 387 IC | Mexico | C | + | + | ND | – |
| Normal | U.S.A. | — | – | – | – | – |

[1]A = acute;
C = convalescent

E. Producing the 406.3-2 Antigen

The 406.3-2 gt11 plasmid from above was digested with EcoRI and the released HEV fragment was amplified by PCR in the presence of linkers which added an NcoI site at the 5' fragment end, and a BamHI site at the 3' fragment end. The amplified material was digested with NcoI and BamHI and inserted into the NcoI/BamHI site of the glutathione S-transferase vector pGEX expression vector, according to the manufacturer's instructions.

The pGEX plasmid was used to transform *E.coli* host cells, and cells which were successfully transformed with the pGEX vector were identified by immunofluorescence, using anti-HEV human antisera.

F. Producing the 406.4-2 Antigen

The 406.4-2 gt11 plasmid from above was digested with EcoRI and the released HEV fragment was amplified by PCR, and the amplified fragment was inserted into the NcoI/BamHI site of the PGEX expression vector, as above. Peptide expression of the 406.4-2 peptide was similar to that described for the 406.3.2 fusion peptide.

G. Preparing Antibodies

The 406.3-2(M) and 406.4-2(M) fusion proteins, prepared as above, were used to immunize rabbits to generate HEV-specific antisera, according to standard procedures.

EXAMPLE 4

Neutralizing Activity of Anti-3.2(M) Antibody

A. In vitro Infection

To prove that primary human hepatocytes were permissive for HEV infection and replication, cells were exposed to either normal human serum (NIH normal human serum pool) or HEV-infected cynomolgus macaque stool preparation (cyno#73). Fourteen days postinfection, total cellular RNAs were prepared for reverse-transcription (RT)/polymerase chain reaction (PCR) assays to evaluate the infectability of primary human hepatocytes with HEV. The results indicated that primary human hepatocytes were capable of supporting HEV propagation (FIG. 4).

Although quantitative PCR was not applied, total cellular RNA isolated from HEV-infected primary human hepatocytes would indicate a high level of virus replication as suggested by the extent of hybridization with the $\alpha$-$^{32}$P-dCTP labeled HEV-specific probe (lane 5). There was no evidence of HEV in total cellular RNA isolated from primary human hepatocytes treated with normal human serum pool (lane 4). As negative controls for RT/PCR assays, no carry-over or cross-contamination was detected (lanes 1, 2, and 3). The original HEV-infected cynomolgus macaque stool (cyno#73) was served as a positive control in the RT/PCR assays (lane 6).

B. Neutralizing Activity of Antibody

To examine the neutralizing activities of anti-3-2(M), -4-2-(M), each rabbit antiserum was used at a final dilution of 1:20 with the viral inoculum for HEV infection of primary human hepatocytes. The diluted antibody and viral inoculum were incubated together prior to infection of the cultured cells. Rabbit anti-3-2(M) exhibited a high level of neutralizing activity against HEV infection (FIG. 5, lane 2 versus lane 1). Very little neutralizing activity was observed in rabbit anti-4-2(M) (lane 4 versus lane 3).

This result suggests that the HEV 3-2(M) but not HEV 4-2(M) or 4-2(B) recombinant protein encoded a neutralizing epitope capable of eliciting protective antibody or antibodies against HEV infection. The fact that the Mexico clone 3-2(M) and the Burma clone 3-2(B) share 90.5% homology at the amino acid level (79.8% at the nucleotide level) suggested that antibody(ies) raised against 3-2(M) should cross-neutralize or cross-protect HEV of Mexico or Burma strain from infecting permissive cells.

EXAMPLE 5

Neutralizing Activity of Anti-3-2(B) and Anti-4-2 (B)

HEV type-common epitopes 3-2 and 4-2 of Burma (B) or Mexico (M) strains were previously identified by screening high titer lambda library for HEV-specific antigen-producing clones using convalescent human serum F387-C. The lambda gt11 clones, 406.3-2 and 406.4-2, were characterized and subcloned to express as betagalactosidase fusion proteins. These fusion proteins were subsequently used to immunize rabbits to generate HEV-specific antisera.

Figure 10A:
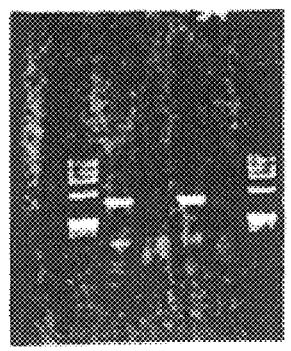
FIG. 10 shows in panel A, the ethidium bromide stained gel of DNA produced from PCR-amplified RNA. The RNA was from HEV infected primary cynomolgus macaque hepatocytes in which the infective virus HEV Burma was preincubated with normal preimmune rabbit serum as shown in lanes 1 and 3; or with rabbit anti-serum against HEV antigen 406.3-2(B) (lane 2), or with HEV 406.4-2(B)(lane 4); panel B shows Southern Blots of the materials as described above in panel A for lanes 1–4.
Figure 10B:
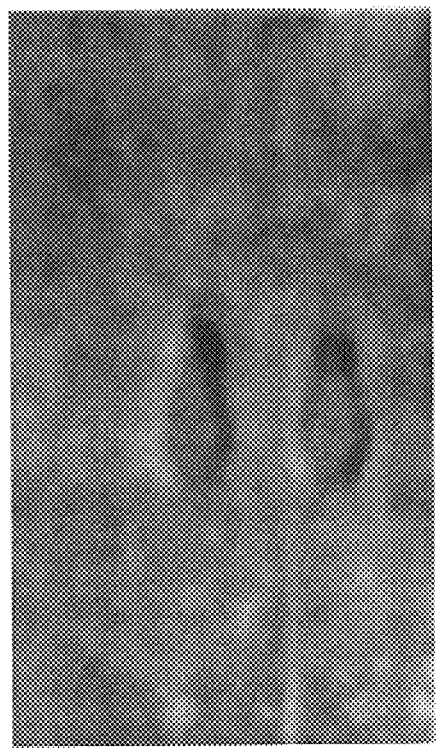

To examine the neutralizing activities of anti-3-2(B) and anti-4-2(B), preimmune rabbit serum or rabbit anti-3-2(B) or anti-4-2(B) antiserum was used at a final dilution of 1:20 with the viral inoculum of Burma strain for HEV invection of primary cynomolgus macaque hepatocytes. Both rabbit anti-3-2(B) (FIG. 10, lane 2) and anti-4-2(B) (FIG. 10, lane 4) but not rabbit preimmune serum (FIG. 10, lane 1 or lane 3) exhibited extraordinary levels of neutralizing activity against HEV infection as indicated by RT/PCR analysis (FIG. 10 panels A and B). This result indicated that both HEV 3-2(B)(Sequence ID No. 13) and HEV 4-2(B) (Sequence ID No. 22) recombinant proteins encode a neutralizing epitope capable of eliciting protective antibody or antibodies against HEV infection. The neutralizing activity of anti-4-2(B) was previously not shown. Therefore, in a cynomologus macaque hepatocyte system it has now been shown that rabbit anti-4-2(B) antibody will neutralize HEV. Thus, the HEV protein designated by sequence ID No 22 is suitable as an immunogen against HEV.

EXAMPLE 6

Vaccine Protection Against HEV

A. Preparation of trpE-C2 peptide

The pBET1 plasmid containing a 2.3 kb insert, corresponding to the 1.8 kb 3' end portion of HEV has been described (Tam). The plasmid was digested with EcoRI, releasing two HEV fragments having sizes of about 600 bp and 1400 bp of which 1210 bp contain coding sequence. The larger fragment was purified by electrophoresis and inserted into the EcoRI site of the pATH10 trpE fusion vector, obtained from T. J. Koerner et al. (Department of Microbiology, UCLA). The recombinant vector was used to transform *E. coli* DH5αF'host.

The recombinant typE-C2 fusion protein from pATH C2 was isolated by a modification of the procedure of Dieckmann et al. The bacterium containing the pATH C2 plasmid was grown overnight in growth media containing tryptophane. Two ml of the overnight culture was inoculated into 100 ml of fresh growth media and grown at 37° C. for an additional four hours. The bacterial broth was added to one liter of fresh growth media without tryptophane and allowed to grow at 30° C. for 1.5 hours. Ten ml indoleacrylic acid (1 mg/ml) was added and growth was continued for an additional 5 to 10 hours at 30° C. The bacterial cells were collected by centrifugation. The cell pellet was resuspended in a hypotonic solution containing lysozyme to degrade the bacterial cell wall. Sodium chloride and the detergent "NP-40" were added to the suspension to cause hypertonic lysis of the cells. The lysed cell solution was sonicated. The solution was centrifuged. The resulting protein pellet was resuspended in about 5 ml of 10 mM Tris pH 7.5 using a dounce homogenizer. Approximately 75% of the protein in solution was composed of the trpE-C2 protein.

B. Preparation of Vaccine

Converted alum adjuvant was prepared according to standard methods. Briefly, a 10% alum suspension was titrated to pH 6.6 with 1N NaOH, then stirred overnight at 4° C. The suspension is clarified by low-speed centrifugation, and the supernatant decanted. A small amount of 0.9% NaCl+1:20,000 formalin was added to each pellet, and suspended by vortexing. To prepare an antigen vaccine composition, trpE-C2 fusion protein from above is added in a 0.9% NaCl solution to a desired final antigen concentration.

A non-adjuvanted insoluble trpE-C2 peptide was prepared as above in section A.

C. Vaccination

Six cynomolgus monkeys, designated 8901, 8902, 8903, 8910, 9902, and 9904, were used in the vaccination study. Four of the monkeys, 8901, and 8902 8903, and 8910 were immunized by intravenous injection with 1.0 ml of the alum adjuvanted trpE-C2 composition (containing about 50 μg of C2 peptide). The other two animals received adjuvant only. One month later the six animals were given a second vaccination, identical to the first. 4 weeks after the second vaccination, saer from the animals was tested for anti-HEV antibodies by Western blotting, using a fusionless C2 protein. At this stage, animals 8901 and 8902 each received a third vaccination with the non-adjuvanted, insoluble trpE-C2 composition (a total IV dose of about 80 μg trpE-C2 peptide each), and both animals showed anti-HEV by Western blotting 4 weeks later.

Animals 8901, 8903, and 9002 were each challenged IV with 1 ml each of a 10% third passage cyno stool (Burma strain) previously shown to be highly infectious. Animals 8902, 8910, and 9004 were each challenged IV with 1 ml of a proven infectious human stool isolate, Mexican #14, known to cause severe disease in cynos and moderate disease in chimpanzees. The results are shown in FIGS. 2A, 2B, and 3A, and 3B, discussed above.

While the invention has been described with reference to particular embodiments, methods, construction and use, it will be apparent to those skilled in the art that various changes and modifications can be made without departing from the invention.

It is claimed:

1. A method of preventing or treating Hepatitis E Virus (HEV) infection in an individual, comprising
administering to the individual, by parenteral injection, a vaccine composition containing antibodies capable of neutralizing HEV infection, as evidenced by the ability of the composition to block HEV infection of primary human hepatocyte cells in culture, and where said composition contains an antibody which is immunoreactive with a peptide containing the C-terminal 48 amino acids of the capsid protein encoded by the second open reading frame of the HEV genome.

2. A method of claim 1, where said vaccine composition contains an antibody which is immunoreactive with a peptide containing one of the sequences:

(i) Sequence ID No. 13,
(ii) Sequence ID No. 14,
(iii) Sequence ID No. 15,
(iv) Sequence ID No. 16,
(v) Sequence ID No. 17,
(vi) Sequence ID No. 18,
(vii) Sequence ID No. 19, and
(viii) Sequence ID No. 20.

3. A method of claim 2, wherein the antibody composition includes an antibody which is immunoreactive against a peptide having the amino acid sequence identified by one of the following sequences:

(v) Sequence ID No. 17, or
(vi) Sequence ID No. 18.

4. A method of claim 2, wherein the antibody composition contains an antibody which is immunoreactive with a peptide containing one of the sequences:

(i) Sequence ID No. 13, or
(ii) Sequence ID No. 14,and one of sequences:
(iii) Sequence ID No. 15, or
(iv) Sequence ID No. 16.

5. A method of claim 4, wherein the antibody in the composition is immunoreactive with a peptide containing the sequence identified by Sequence ID No. 15.

* * * * *

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 2094 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (vi) ORIGINAL SOURCE:
      (C) INDIVIDUAL ISOLATE: BURMA SEQUENCE, FIGURE 7

(xi) SEQUENCE DESCRIPTION: SEQ ID NO:1:

```
TGGAATGAAT AACATGTCTT TTGCTGCGCC CATGGGTTCG CGACCATGCG CCCTCGGCCT      60

ATTTTGTTGC TGCTCCTCAT GTTTTTGCCT ATGCTGCCCG CGCCACCGCC CGGTCAGCCG     120

TCTGGCCGCC GTCGTGGGCG GCGCAGCGGC GGTTCCGGCG GTGGTTTCTG GGGTGACCGG     180

GTTGATTCTC AGCCCTTCGC AATCCCCTAT ATTCATCCAA CCAACCCCTT CGCCCCCGAT     240

GTCACCGCTG CGGCCGGGGC TGGACCTCGT GTTCGCCAAC CCGCCCGACC ACTCGGCTCC     300

GCTTGGCGTG ACCAGGCCCA GCGCCCCGCC GTTGCCTCAC GTCGTAGACC TACCACAGCT     360

GGGGCCGCGC CGCTAACCGC GGTCGCTCCG GCCCATGACA CCCCGCCAGT GCCTGATGTC     420

GACTCCCGCG GCGCCATCTT GCGCCGGCAG TATAACCTAT CAACATCTCC CCTTACCTCT     480

TCCGTGGCCA CCGGCACTAA CCTGGTTCTT TATGCCGCCC CTCTTAGTCC GCTTTTACCC     540

CTTCAGGACG GCACCAATAC CCATATAATG GCCACGGAAG CTTCTAATTA TGCCCAGTAC     600

CGGGTTGCCC GTGCCACAAT CCGTTACCGC CCGCTGGTCC CCAATGCTGT CGGCGGTTAC     660

GCCATCTCCA TCTCATTCTG GCCACAGACC ACCACCACCC CGACGTCCGT TGATATGAAT     720

TCAATAACCT CGACGGATGT TCGTATTTTA GTCCAGCCCG GCATAGCCTC TGAGCTTGTG     780

ATCCCAAGTG AGCGCCTACA CTATCGTAAC CAAGGCTGGC GCTCCGTCGA GACCTCTGGG     840

GTGGCTGAGG AGGAGGCTAC CTCTGGTCTT GTTATGCTTT GCATACATGG CTCACTCGTA     900

AATTCCTATA CTAATACACC CTATACCGGT GCCCTCGGGC TGTTGGACTT TGCCCTTGAG     960

CTTGAGTTTC GCAACCTTAC CCCCGGTAAC ACCAATACGC GGGTCTCCCG TTATTCCAGC    1020

ACTGCTCGCC ACCGCCTTCG TCGCGGTGCG GACGGGACTG CCGAGCTCAC CACCACGGCT    1080

GCTACCCGCT TTATGAAGGA CCTCTATTTT ACTAGTACTA ATGGTGTCGG TGAGATCGGC    1140

CGCGGGATAG CCCTCACCCT GTTCAACCTT GCTGACACTC TGCTTGGCGG CCTGCCGACA    1200
```

-continued

```
GAATTGATTT CGTCGGCTGG TGGCCAGCTG TTCTACTCCC GTCCCGTTGT CTCAGCCAAT    1260

GGCGAGCCGA CTGTTAAGTT GTATACATCT GTAGAGAATG CTCAGCAGGA TAAGGGTATT    1320

GCAATCCCGC ATGACATTGA CCTCGGAGAA TCTCGTGTGG TTATTCAGGA TTATGATAAC    1380

CAACATGAAC AAGATCGGCC GACGCCTTCT CCAGCCCCAT CGCGCCCTTT CTCTGTCCTT    1440

CGAGCTAATG ATGTGCTTTG GCTCTCTCTC ACCGCTGCCG AGTATGACCA GTCCACTTAT    1500

GGCTCTTCGA CTGGCCCAGT TTATGTTTCT GACTCTGTGA CCTTGGTTAA TGTTGCGACC    1560

GGCGCGCAGG CCGTTGCCCG GTCGCTCGAT TGGACCAAGG TCACACTTGA CGGTCGCCCC    1620

CTCTCCACCA TCCAGCAGTA CTCGAAGACC TTCTTTGTCC TGCCGCTCCG CGGTAAGCTC    1680

TCTTTCTGGG AGGCAGGCAC AACTAAAGCC GGGTACCCTT ATAATTATAA CACCACTGCT    1740

AGCGACCAAC TGCTTGTCGA GAATGCCGCC GGGCACCGGG TCGCTATTTC CACTTACACC    1800

ACTAGCCTGG GTGCTGGTCC CGTCTCCATT TCTGCGGTTG CCGTTTTAGC CCCCCACTCT    1860

GCGCTAGCAT TGCTTGAGGA TACCTTGGAC TACCCTGCCC GCGCCCATAC TTTTGATGAT    1920

TTCTGCCCAG AGTGCCGCCC CCTTGGCCTT CAGGGCTGCG CTTTCCAGTC TACTGTCGCT    1980

GAGCTTCAGC GCCTTAAGAT GAAGGTGGGT AAAACTCGGG AGTTGTAGTT TATTTGCTTG    2040

TGCCCCCCTT CTTTCTGTTG CTTATTTCTC ATTTCTGCGT TCCGCGCTCC CTGA          2094

(2) INFORMATION FOR SEQ ID NO:2:

(i) SEQUENCE CHARACTERISTICS:
        (A) LENGTH: 2100 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (vi) ORIGINAL SOURCE:
        (C) INDIVIDUAL ISOLATE: MEXICO, FIGURE 7

(xi) SEQUENCE DESCRIPTION: SEQ ID NO:2:

CTGAATGAAT AACATGTGGT TTGCTGCGCC CATGGGTTCG CCACCATGCG CCCTAGGCCT      60

CTTTTGCTGT TGTTCCTCTT GTTTCTGCCT ATGTTGCCCG CGCCACCGAC CGGTCAGCCG     120

TCTGGCCGCC GTCGTGGGCG GCGCAGCGGC GGTACCGGCG GTGGTTTCTG GGGTGACCGG     180

GTTGATTCTC AGCCCTTCGC AATCCCCTAT ATTCATCCAA CCAACCCCTT TGCCCCAGAC     240

GTTGCCGCTG CGTCCGGGTC TGGACCTCGC CTTCGCCAAC CAGCCCGGCC ACTTGGCTCC     300

ACTTGGCGAG ATCAGGCCCA GCGCCCCTCC GCTGCCTCCC GTCGCCGACC TGCCACAGCC     360

GGGGCTGCGG CGCTGACGGC TGTGGCGCCT GCCCATGACA CCTCACCCGT CCCGGACGTT     420

GATTCTCGCG GTGCAATTCT ACGCCGCCAG TATAATTTGT CTACTTCACC CCTGACATCC     480

TCTGTGGCCT CTGGCACTAA TTTAGTCCTG TATGCAGCCC CCCTTAATCC GCCTCTGCCG     540

CTGCAGGACG GTACTAATAC TCACATTATG GCCACAGAGG CCTCCAATTA TGCACAGTAC     600

CGGGTTGCCC GCGCTACTAT CCGTTACCGG CCCCTAGTGC CTAATGCAGT TGGAGGCTAT     660

GCTATATCCA TTTCTTTCTG GCCTCAAACA ACCACAACCC CTACATCTGT TGACATGAAT     720

TCCATTACTT CCACTGATGT CAGGATTCTT GTTCAACCTG GCATAGCATC TGAATTGGTC     780

ATCCCAAGCG AGCGCCTTCA CTACCGCAAT CAAGGTTGGC GCTCGGTTGA CATCTGGT      840

GTTGCTGAGG AGGAAGCCAC CTCCGGTCTT GTCATGTTAT GCATACATGG CTCTCCAGTT     900

AACTCCTATA CCAATACCCC TTATACCGGT GCCCTTGGCT TACTGGACTT TGCCTTAGAG     960
```

```
CTTGAGTTTC GCAATCTCAC CACCTGTAAC ACCAATACAC GTGTGTCCCG TTACTCCAGC    1020

ACTGCTCGTC ACTCCGCCCG AGGGGCCGAC GGGACTGCGG AGCTGACCAC AACTGCAGCC    1080

ACCAGGTTCA TGAAAGATCT CCACTTTACC GGCCTTAATG GGGTAGGTGA AGTCGGCCGC    1140

GGGATAGCTC TAACATTACT TAACCTTGCT GACACGCTCC TCGGCGGGCT CCCGACAGAA    1200

TTAATTTCGT CGGCTGGCGG GCAACTGTTT TATTCCCGCC CGGTTGTCTC AGCCAATGGC    1260

GAGCCAACCG TGAAGCTCTA TACATCAGTG GAGAATGCTC AGCAGGATAA GGGTGTTGCT    1320

ATCCCCCACG ATATCGATCT TGGTGATTCG CGTGTGGTCA TTCAGGATTA TGACAACCAG    1380

CATGAGCAGG ATCGGCCCAC CCCGTCGCCT GCGCCATCTC GGCCTTTTTC TGTTCTCCGA    1440

GCAAATGATG TACTTTGGCT GTCCCTCACT GCAGCCGAGT ATGACCAGTC CACTTACGGG    1500

TCGTCAACTG GCCCGGTTTA TATCTCGGAC AGCGTGACTT TGGTGAATGT TGCGACTGGC    1560

GCGCAGGCCG TAGCCCGATC GCTTGACTGG TCCAAAGTCA CCCTCGACGG GCGGCCCCTC    1620

CCGACTGTTG AGCAATATTC AAGACATTC TTTGTGCTCC CCCTTCGTGG CAAGCTCTCC     1680

TTTTGGGAGG CCGGCACAAC AAAAGCAGGT TATCCTTATA ATTATAATAC TACTGCTAGT    1740

GACCAGATTC TGATTGAAAA TGCTGCCGGC CATCGGGTCG CCATTTCAAC CTATACCACC    1800

AGGCTTGGGG CCGGTCCGGT CGCCATTTCT GCGGCCGCGG TTTTGGCTCC ACGCTCCGCC    1860

CTGGCTCTGC TGGAGGATAC TTTTGATTAT CCGGGGCGGG CGCACACATT TGATGACTTC    1920

TGCCCTGAAT GCCGCGCTTT AGGCCTCCAG GGTTGTGCTT TCCAGTCAAC TGTCGCTGAG    1980

CTCCAGCGCC TTAAAGTTAA GGTGGGTAAA ACTCGGGAGT TGTAGTTTAT TTGGCTGTGC    2040

CCACCTACTT ATATCTGCTG ATTTCCTTTA TTTCCTTTTT CTCGGTCCCG CGCTCCCTGA    2100

(2) INFORMATION FOR SEQ ID NO:3:

(i) SEQUENCE CHARACTERISTICS:
        (A) LENGTH: 2049 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (vi) ORIGINAL SOURCE:
         (C) INDIVIDUAL ISOLATE: ORF 2, BURMA, FIGURE 7

(xi) SEQUENCE DESCRIPTION: SEQ ID NO:3:

ATGCGCCCTC GGCCTATTTT GTTGCTGCTC CTCATGTTTT TGCCTATGCT GCCCGCGCCA      60

CCGCCCGGTC AGCCGTCTGG CCGCCGTCGT GGGCGGCGCA GCGGCGGTTC CGGCGGTGGT     120

TTCTGGGGTG ACCGGGTTGA TTCTCAGCCC TTCGCAATCC CCTATATTCA TCCAACCAAC     180

CCCTTCGCCC CCGATGTCAC CGCTGCGGCC GGGGCTGGAC CTCGTGTTCG CCAACCCGCC     240

CGACCACTCG GCTCCGCTTG GCGTGACCAG GCCCAGCGCC CCGCCGTTGC CTCACGTCGT     300

AGACCTACCA CAGCTGGGGC CGCGCCGCTA ACCGCGGTCG CTCCGGCCCA TGACACCCCG     360

CCAGTGCCTG ATGTCGACTC CCGCGGCGCC ATCTTGCGCC GGCAGTATAA CCTATCAACA     420

TCTCCCCTTA CCTCTTCCGT GGCCACCGGC ACTAACCTGG TTCTTTATGC CGCCCCTCTT     480

AGTCCGCTTT TACCCCTTCA GGACGGCACC AATACCCATA TAATGGCCAC GGAAGCTTCT     540

AATTTATGCC AGTACCGGGT TGCCCGTGCC ACAATCCGTT ACCGCCCGCT GGTCCCCAAT     600

GCTGTCGGCG GTTACGCCAT CTCCATCTCA TTCTGGCCAC AGACCACCAC CACCCCGACG     660
```

```
TCCGTTGATA TGAATTCAAT AACCTCGACG GATGTTCGTA TTTTAGTCCA GCCCGGCATA      720

GCCTCTGAGC TTGTGATCCC AAGTGAGCGC CTACACTATC GTAACCAAGG CTGGCGCTCC      780

GTCGAGACCT CTGGGGTGGC TGAGGAGGAG GCTACCTCTG GTCTTGTTAT GCTTTGCATA      840

CATGGCTCAC TCGTAAATTC CTATACTAAT ACACCCTATA CCGGTGCCCT CGGGCTGTTG      900

GACTTTGCCC TTGAGCTTGA GTTTCGCAAC CTTACCCCCG GTAACACCAA TACGCGGGTC      960

TCCCGTTATT CCAGCACTGC TCGCCACCGC CTTCGTCGCG GTGCGGACGG GACTGCCGAG     1020

CTCACCACCA CGGCTGCTAC CCGCTTTATG AAGGACCTCT ATTTTACTAG TACTAATGGT     1080

GTCGGTGAGA TCGGCCGCGG GATAGCCCTC ACCCTGTTCA ACCTTGCTGA CACTCTGCTT     1140

GGCGGCCTGC CGACAGAATT GATTTCGTCG GCTGGTGGCC AGCTGTTCTA CTCCCGTCCC     1200

GTTGTCTCAG CCAATGGCGA GCCGACTGTT AAGTTGTATA CATCTGTAGA GAATGCTCAG     1260

CAGGATAAGG GTATTGCAAT CCCGCATGAC ATTGACCTCG GAGAATCTCG TGTGGTTATT     1320

CAGGATTATG ATAACCAACA TGAACAAGAT CGGCCGACGC CTTCTCCAGC CCCATCGCGC     1380

CCTTTCTCTG TCCTTCGAGC TAATGATGTG CTTTGGCTCT CTCTCACCGC TGCCGAGTAT     1440

GACCAGTCCA CTTATGGCTC TTCGACTGGC CCAGTTTATG TTTCTGACTC TGTGACCTTG     1500

GTTAATGTTG CGACCGGCGC GCAGGCCGTT GCCCGGTCGC TCGATTGGAC CAAGGTCACA     1560

CTTGACGGTC GCCCCCTCTC CACCATCCAG CAGTACTCGA AGACCTTCTT TGTCCTGCCG     1620

CTCCGCGGTA AGCTCTCTTT CTGGGAGGCA GGCACAACTA AAGCCGGGTA CCCTTATAAT     1680

TATAACACCA CTGCTAGCGA CCAACTGCTT GTCGAGAATG CCGCCGGGCA CCGGGTCGCT     1740

ATTTCCACTT ACACCACTAG CCTGGGTGCT GGTCCCGTCT CCATTTCTGC GGTTGCCGTT     1800

TTAGCCCCCC ACTCTGCGCT AGCATTGCTT GAGGATACCT TGGACTACCC TGCCCGCGCC     1860

CATACTTTTG ATGATTTCTG CCCAGAGTGC CGCCCCCTTG GCCTTCAGGG CTGCGCTTTC     1920

CAGTCTACTG TCGCTGAGCT TCAGCGCCTT AAGATGAAGG TGGGTAAAAC TCGGGAGTTG     1980

TAGTTTATTT GCTTGTGCCC CCCTTCTTTC TGTTGCTTAT TTCTCATTTC TGCGTTCCGC     2040

GCTCCCTGA                                                            2049

(2) INFORMATION FOR SEQ ID NO:4:

(i) SEQUENCE CHARACTERISTICS:
        (A) LENGTH: 2055 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (vi) ORIGINAL SOURCE:
        (C) INDIVIDUAL ISOLATE: ORF 2, MEXICO, FIGURE 7

(xi) SEQUENCE DESCRIPTION: SEQ ID NO:4:

ATGCGCCCTA GGCCTCTTTT GCTGTTGTTC CTCTTGTTTC TGCCTATGTT GCCCGCGCCA       60

CCGACCGGTC AGCCGTCTGG CCGCCGTCGT GGGCGGCGCA GCGGCGGTAC CGGCGGTGGT      120

TTCTGGGGTG ACCGGGTTGA TTCTCAGCCC TTCGCAATCC CCTATATTCA TCCAACCAAC      180

CCCTTTGCCC CAGACGTTGC CGCTGCGTCC GGGTCTGGAC CTCGCCTTCG CCAACCAGCC      240

CGGCCACTTG GCTCCACTTG GCGAGATCAG GCCCAGCGCC CCTCCGCTGC CTCCCGTCGC      300

CGACCTGCCA CAGCCGGGGC TGCGGCGCTG ACGGCTGTGG CGCCTGCCCA TGACACCTCA      360

CCCGTCCCGG ACGTTGATTC TCGCGGTGCA ATTCTACGCC GCCAGTATAA TTTGTCTACT      420
```

```
TCACCCCTGA CATCCTCTGT GGCCTCTGGC ACTAATTTAG TCCTGTATGC AGCCCCCCTT      480

AATCCGCCTC TGCCGCTGCA GGACGGTACT AATACTCACA TTATGGCCAC AGAGGCCTCC      540

AATTATGCAC AGTACCGGGT TGCCCGCGCT ACTATCCGTT ACCGGCCCCT AGTGCCTAAT      600

GCAGTTGGAG CTATGCTAT ATCCATTTCT TTCTGGCCTC AAACAACCAC AACCCCTACA      660

TCTGTTGACA TGAATTCCAT TACTTCCACT GATGTCAGGA TTCTTGTTCA ACCTGGCATA      720

GCATCTGAAT TGGTCATCCC AAGCGAGCGC CTTCACTACC GCAATCAAGG TTGGCGCTCG      780

GTTGAGACAT CTGGTGTTGC TGAGGAGGAA GCCACCTCCG GTCTTGTCAT GTTATGCATA      840

CATGGCTCTC CAGTTAACTC CTATACCAAT ACCCCTTATA CCGGTGCCCT TGGCTTACTG      900

GACTTTGCCT TAGAGCTTGA GTTTCGCAAT CTCACCACCT GTAACACCAA TACACGTGTG      960

TCCCGTTACT CCAGCACTGC TCGTCACTCC GCCCGAGGGG CCGACGGGAC TGCGGAGCTG     1020

ACCACAACTG CAGCCACCAG GTTCATGAAA GATCTCCACT TTACCGGCCT TAATGGGGTA     1080

GGTGAAGTCG GCCGCGGGAT AGCTCTAACA TTACTTAACC TTGCTGACAC GCTCCTCGGC     1140

GGGCTCCCGA CAGAATTAAT TTCGTCGGCT GGCGGGCAAC TGTTTTATTC CCGCCCGGTT     1200

GTCTCAGCCA ATGGCGAGCC AACCGTGAAG CTCTATACAT CAGTGGAGAA TGCTCAGCAG     1260

GATAAGGGTG TTGCTATCCC CCACGATATC GATCTTGGTG ATTCGCGTGT GGTCATTCAG     1320

GATTATGACA ACCAGCATGA GCAGGATCGG CCCACCCCGT CGCCTGCGCC ATCTCGGCCT     1380

TTTTCTGTTC TCCGAGCAAA TGATGTACTT TGGCTGTCCC TCACTGCAGC CGAGTATGAC     1440

CAGTCCACTT ACGGGTCGTC AACTGGCCCG GTTTATATCT CGGACAGCGT GACTTTGGTG     1500

AATGTTGCGA CTGGCGCGCA GGCCGTAGCC CGATCGCTTG ACTGGTCCAA AGTCACCCTC     1560

GACGGGCGGC CCCTCCCGAC TGTTGAGCAA TATTCCAAGA CATTCTTTGT GCTCCCCCTT     1620

CGTGGCAAGC TCTCCTTTTG GGAGGCCGGC ACAACAAAAG CAGGTTATCC TTATAATTAT     1680

AATACTACTG CTAGTGACCA GATTCTGATT GAAAATGCTG CCGGCCATCG GGTCGCCATT     1740

TCAACCTATA CCACCAGGCT TGGGGCCGGT CCGGTCGCCA TTTCTGCGGC CGCGGTTTTG     1800

GCTCCACGCT CCGCCCTGGC TCTGCTGGAG GATACTTTTG ATTATCCGGG GCGGGCGCAC     1860

ACATTTGATG ACTTCTGCCC TGAATGCCGC GCTTTAGGCC TCCAGGGTTG TGCTTTCCAG     1920

TCAACTGTCG CTGAGCTCCA GCGCCTTAAA GTTAAGGTGG GTAAAACTCG GGAGTTGTAG     1980

TTTATTTGGC TGTGCCCACC TACTTATATC TGCTGATTTC CTTTATTTCC TTTTTCTCGG     2040

TCCCGCGCTC CCTGA                                                     2055
```

(2) INFORMATION FOR SEQ ID NO:5:

(i) SEQUENCE CHARACTERISTICS:
        (A) LENGTH: 147 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (vi) ORIGINAL SOURCE:
        (C) INDIVIDUAL ISOLATE: 406.3-2, BURMA, FIGURE 7

(xi) SEQUENCE DESCRIPTION: SEQ ID NO:5:

```
ACCTTGGACT ACCCTGCCCG CGCCCATACT TTTGATGATT TCTGCCCAGA GTGCCGCCCC       60

CTTGGCCTTC AGGGCTGCGC TTTCCAGTCT ACTGTCGCTG AGCTTCAGCG CCTTAAGATG      120
```

```
AAGGTGGGTA AAACTCGGGA GTTGTAG                                          147
```

(2) INFORMATION FOR SEQ ID NO:6:

(i) SEQUENCE CHARACTERISTICS:
        (A) LENGTH: 147 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (vi) ORIGINAL SOURCE:
        (C) INDIVIDUAL ISOLATE: 406.3-2, MEXICO, FIGURE 7

(xi) SEQUENCE DESCRIPTION: SEQ ID NO:6:

```
ACTTTTGATT ATCCGGGGCG GGCGCACACA TTTGATGACT TCTGCCCTGA ATGCCGCGCT    60
TTAGGCCTCC AGGGTTGTGC TTTCCAGTCA ACTGTCGCTG AGCTCCAGCG CCTTAAAGTT   120
AAGGTGGGTA AAACTCGGGA GTTGTAG                                       147
```

(2) INFORMATION FOR SEQ ID NO:7:

(i) SEQUENCE CHARACTERISTICS:
        (A) LENGTH: 984 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (vi) ORIGINAL SOURCE:
        (C) INDIVIDUAL ISOLATE: SG3, BURMA, FIGURE 7

(xi) SEQUENCE DESCRIPTION: SEQ ID NO:7:

```
GGTGCGGACG GGACTGCCGA GCTCACCACC ACGGCTGCTA CCCGCTTTAT GAAGGACCTC    60
TATTTTACTA GTACTAATGG TGTCGGTGAG ATCGGCCGCG GGATAGCCCT CACCCTGTTC   120
AACCTTGCTG ACACTCTGCT TGGCGGCCTG CCGACAGAAT TGATTTCGTC GGCTGGTGGC   180
CAGCTGTTCT ACTCCCGTCC CGTTGTCTCA GCCAATGGCG AGCCGACTGT TAAGTTGTAT   240
ACATCTGTAG AGAATGCTCA GCAGGATAAG GGTATTGCAA TCCCGCATGA CATTGACCTC   300
GGAGAATCTC GTGTGGTTAT TCAGGATTAT GATAACCAAC ATGAACAAGA TCGGCCGACG   360
CCTTCTCCAG CCCCATCGCG CCCTTTCTCT GTCCTTCGAG CTAATGATGT GCTTTGGCTC   420
TCTCTCACCG CTGCCGAGTA TGACCAGTCC ACTTATGGCT CTTCGACTGG CCCAGTTTAT   480
GTTTCTGACT CTGTGACCTT GGTTAATGTT GCGACCGGCG CGCAGGCCGT TGCCCGGTCG   540
CTCGATTGGA CCAAGGTCAC ACTTGACGGT CGCCCCCTCT CCACCATCCA GCAGTACTCG   600
AAGACCTTCT TTGTCCTGCC GCTCCGCGGT AAGCTCTCTT TCTGGGAGGC AGGCACAACT   660
AAAGCCGGGT ACCCTTATAA TTATAACACC ACTGCTAGCG ACCAACTGCT TGTCGAGAAT   720
GCCGCCGGGC ACCGGGTCGC TATTTCCACT TACACCACTA GCCTGGGTGC TGGTCCCGTC   780
TCCATTTCTG CGGTTGCCGT TTTAGCCCCC CACTCTGCGC TAGCATTGCT TGAGGATACC   840
TTGGACTACC CTGCCCGCGC CCATACTTTT GATGATTTCT GCCCAGAGTG CCGCCCCCTT   900
GGCCTTCAGG GCTGCGCTTT CCAGTCTACT GTCGCTGAGC TTCAGCGCCT TAAGATGAAG   960
GTGGGTAAAA CTCGGGAGTT GTAG                                         984
```

(2) INFORMATION FOR SEQ ID NO:8:

(i) SEQUENCE CHARACTERISTICS:
        (A) LENGTH: 981 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (vi) ORIGINAL SOURCE:
        (C) INDIVIDUAL ISOLATE: SG3, MEXICO, FIGURE 7

(xi) SEQUENCE DESCRIPTION: SEQ ID NO:8:

```
GCCGACGGGA CTGCGGAGCT GACCACAACT GCAGCCACCA GGTTCATGAA AGATCTCCAC      60
TTTACCGGCC TTAATGGGGT AGGTGAAGTC GGCCGCGGGA TAGCTCTAAC ATTACTTAAC     120
CTTGCTGACA CGCTCCTCGG CGGGCTCCCG ACAGAATTAA TTTCGTCGGC TGGCGGGCAA     180
CTGTTTTATT CCCGCCCGGT TGTCTCAGCC AATGGCGAGC CAACCGTGAA GCTCTATACA     240
TCAGTGGAGA ATGCTCAGCA GGATAAGGGT GTTGCTATCC CCACGATAT CGATCTTGGT      300
GATTCGCGTG TGGTCATTCA GGATTATGAC AACCAGCATG AGCAGGATCG GCCCACCCCG     360
TCGCCTGCGC CATCTCGGCC TTTTTCTGTT CTCCGAGCAA ATGATGTACT TTGGCTGTCC     420
CTCACTGCAG CCGAGTATGA CCAGTCCACT TACGGGTCGT CAACTGGCCC GGTTTATATC     480
TCGGACAGCG TGACTTTGGT GAATGTTGCG ACTGGCGCGC AGGCCGTAGC CCGATCGCTT     540
GACTGGTCCA AAGTCACCCT CGACGGGCGG CCCCTCCCGA CTGTTGAGCA ATATTCCAAG     600
ACATTCTTTG TGCTCCCCCT TCGTGGCAAG CTCTCCTTTT GGGAGGCCGG CACAACAAAA     660
GCAGGTTATC CTTATAATTA TAATACTACT GCTAGTGACC AGATTCTGAT TGAAAATGCT     720
GCCGGCCATC GGGTCGCCAT TTCAACCTAT ACCACCAGGC TTGGGGCCGG TCCGGTCGCC     780
ATTTCTGCGG CCGCGGTTTT GGCTCCACGC TCCGCCCTGG CTCTGCTGGA GGATACTTTT     840
GATTATCCGG GGCGGGCGCA CACATTTGAT GACTTCTGCC CTGAATGCCG CGCTTTAGGC     900
CTCCAGGGTT GTGCTTTCCA GTCAACTGTC GCTGAGCTCC AGCGCCTTAA AGTTAAGGTG     960
GGTAAAACTC GGGAGTTGTA G                                              981
```

(2) INFORMATION FOR SEQ ID NO:9:

(i) SEQUENCE CHARACTERISTICS:
        (A) LENGTH: 1311 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (vi) ORIGINAL SOURCE:
        (C) INDIVIDUAL ISOLATE: C2, BURMA, FIGURE 7

(xi) SEQUENCE DESCRIPTION: SEQ ID NO:9:

```
AATTCAATAA CCTCGACGGA TGTTCGTATT TTAGTCCAGC CCGGCATAGC CTCTGAGCTT      60
GTGATCCCAA GTGAGCGCCT ACACTATCGT AACCAAGGCT GGCGCTCCGT CGAGACCTCT     120
GGGGTGGCTG AGGAGGAGGC TACCTCTGGT CTTGTTATGC TTTGCATACA TGGCTCACTC     180
GTAAATTCCT ATACTAATAC ACCCTATACC GGTGCCCTCG GGCTGTTGGA CTTTGCCCTT     240
GAGCTTGAGT TTCGCAACCT TACCCCCGGT AACACCAATA CGCGGGTCTC CCGTTATTCC     300
```

-continued

```
AGCACTGCTC GCCACCGCCT TCGTCGCGGT GCGGACGGGA CTGCCGAGCT CACCACCACG    360

GCTGCTACCC GCTTTATGAA GGACCTCTAT TTTACTAGTA CTAATGGTGT CGGTGAGATC    420

GGCCGCGGGA TAGCCCTCAC CCTGTTCAAC CTTGCTGACA CTCTGCTTGG CGGCCTGCCG    480

ACAGAATTGA TTTCGTCGGC TGGTGGCCAG CTGTTCTACT CCCGTCCCGT TGTCTCAGCC    540

AATGGCGAGC CGACTGTTAA GTTGTATACA TCTGTAGAGA ATGCTCAGCA GGATAAGGGT    600

ATTGCAATCC CGCATGACAT TGACCTCGGA GAATCTCGTG TGGTTATTCA GGATTATGAT    660

AACCAACATG AACAAGATCG GCCGACGCCT CTCCAGCCC CATCGCGCCC TTTCTCTGTC     720

CTTCGAGCTA ATGATGTGCT TTGGCTCTCT CTCACCGCTG CCGAGTATGA CCAGTCCACT    780

TATGGCTCTT CGACTGGCCC AGTTTATGTT TCTGACTCTG TGACCTTGGT TAATGTTGCG    840

ACCGGCGCGC AGGCCGTTGC CCGGTCGCTC GATTGGACCA AGGTCACACT TGACGGTCGC    900

CCCCTCTCCA CCATCCAGCA GTACTCGAAG ACCTTCTTTG TCCTGCCGCT CCGCGGTAAG    960

CTCTCTTTCT GGGAGGCAGG CACAACTAAA GCCGGGTACC CTTATAATTA TAACACCACT   1020

GCTAGCGACC AACTGCTTGT CGAGAATGCC GCCGGGCACC GGGTCGCTAT TTCCACTTAC   1080

ACCACTAGCC TGGGTGCTGG TCCCGTCTCC ATTTCTGCGG TTGCCGTTTT AGCCCCCCAC   1140

TCTGCGCTAG CATTGCTTGA GGATACCTTG GACTACCCTG CCCGCGCCCA TACTTTTGAT   1200

GATTTCTGCC CAGAGTGCCG CCCCCTTGGC CTTCAGGGCT GCGCTTTCCA GTCTACTGTC   1260

GCTGAGCTTC AGCGCCTTAA GATGAAGGTG GGTAAAACTC GGGAGTTGTA G            1311
```

(2) INFORMATION FOR SEQ ID NO:10:

(i) SEQUENCE CHARACTERISTICS:
        (A) LENGTH: 1308 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (vi) ORIGINAL SOURCE:
        (C) INDIVIDUAL ISOLATE: C2, MEXICO, FIGURE 7

(xi) SEQUENCE DESCRIPTION: SEQ ID NO:10:

```
AATTCCATTA CTTCCACTGA TGTCAGGATT CTTGTTCAAC CTGGCATAGC ATCTGAATTG     60

GTCATCCCAA GCGAGCGCCT TCACTACCGC AATCAAGGTT GGCGCTCGGT TGAGACATCT    120

GGTGTTGCTG AGGAGGAAGC CACCTCCGGT CTTGTCATGT TATGCATACA TGGCTCTCCA    180

GTTAACTCCT ATACCAATAC CCCTTATACC GGTGCCCTTG GCTTACTGGA CTTTGCCTTA    240

GAGCTTGAGT TTCGCAATCT CACCACCTGT AACACCAATA CACGTGTGTC CCGTTACTCC    300

AGCACTGCTC GTCACTCCGC CCGAGGGGCC GACGGGACTG CGGAGCTGAC CACAACTGCA    360

GCCACCAGGT TCATGAAAGA TCTCCACTTT ACCGGCCTTA ATGGGGTAGG TGAAGTCGGC    420

CGCGGGATAG CTCTAACATT ACTTAACCTT GCTGACACGC TCCTCGGCGG GCTCCCGACA    480

GAATTAATTT CGTCGGCTGG CGGGCAACTG TTTTATTCCC GCCCGGTTGT CTCAGCCAAT    540

GGCGAGCCAA CCGTGAAGCT CTATACATCA GTGGAGAATG CTCAGCAGGA TAAGGGTGTT    600

GCTATCCCCC ACGATATCGA TCTTGGTGAT TCGCGTGTGG TCATTCAGGA TTATGACAAC    660

CAGCATGAGC AGGATCGGCC CACCCCGTCG CCTGCGCCAT CTCGGCCTTT TTCTGTTCTC    720

CGAGCAAATG ATGTACTTTG GCTGTCCCTC ACTGCAGCCG AGTATGACCA GTCCACTTAC    780

GGGTCGTCAA CTGGCCCGGT TTATATCTCG GACAGCGTGA CTTTGGTGAA TGTTGCGACT    840
```

```
GGCGCGCAGG CCGTAGCCCG ATCGCTTGAC TGGTCCAAAG TCACCCTCGA CGGGCGGCCC      900

CTCCCGACTG TTGAGCAATA TTCCAAGACA TTCTTTGTGC TCCCCCTTCG TGGCAAGCTC      960

TCCTTTTGGG AGGCCGGCAC AACAAAAGCA GGTTATCCTT ATAATTATAA TACTACTGCT     1020

AGTGACCAGA TTCTGATTGA AAATGCTGCC GGCCATCGGG TCGCCATTTC AACCTATACC     1080

ACCAGGCTTG GGGCCGGTCC GGTCGCCATT TCTGCGGCCG CGGTTTTGGC TCCACGCTCC     1140

GCCCTGGCTC TGCTGGAGGA TACTTTTGAT TATCCGGGGC GGGCGCACAC ATTTGATGAC     1200

TTCTGCCCTG AATGCCGCGC TTTAGGCCTC CAGGGTTGTG CTTTCCAGTC AACTGTCGCT     1260

GAGCTCCAGC GCCTTAAAGT TAAGGTGGGT AAAACTCGGG AGTTGTAG                  1308

(2) INFORMATION FOR SEQ ID NO:11:

(i) SEQUENCE CHARACTERISTICS:
        (A) LENGTH: 102 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (vi) ORIGINAL SOURCE:
        (C) INDIVIDUAL ISOLATE: 406.4-2, BURMA, FIGURE 7

(xi) SEQUENCE DESCRIPTION: SEQ ID NO:11:

GCCAACCCGC CCGACCACTC GGCTCCGCTT GGCGTGACCA GGCCCAGCGC CCCGCCGTTG       60

CCTCACGTCG TAGACCTACC ACAGCTGGGG CCGCGCCGCT AA                        102

(2) INFORMATION FOR SEQ ID NO:12:

(i) SEQUENCE CHARACTERISTICS:
        (A) LENGTH: 102 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (vi) ORIGINAL SOURCE:
        (C) INDIVIDUAL ISOLATE: 406.4-2, MEXICO, FIGURE 7

(xi) SEQUENCE DESCRIPTION: SEQ ID NO:12:

GCCAACCAGC CCGGCCACTT GGCTCCACTT GGCGAGATCA GGCCCAGCGC CCCTCCGCTG       60

CCTCCCGTCG CCGACCTGCC ACAGCCGGGG CTGCGGCGCT GA                        102

(2) INFORMATION FOR SEQ ID NO:13:

(i) SEQUENCE CHARACTERISTICS:
        (A) LENGTH: 48 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: 406.3-2, BURMA, FIGURE 9

(xi) SEQUENCE DESCRIPTION: SEQ ID NO:13:

Thr Leu Asp Tyr Pro Ala Arg Ala His Thr Phe Asp Asp Phe Cys Pro
```

```
        1               5                   10                  15
Glu Cys Arg Pro Leu Gly Leu Gln Gly Cys Ala Phe Gln Ser Thr Val
                20                  25                  30

Ala Glu Leu Gln Arg Leu Lys Met Lys Val Gly Lys Thr Arg Glu Leu
                35                  40                  45
```

(2) INFORMATION FOR SEQ ID NO:14:

(i) SEQUENCE CHARACTERISTICS:
        (A) LENGTH: 48 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: 406.3-2, MEXICO, FIGURE 9

(xi) SEQUENCE DESCRIPTION: SEQ ID NO:14:

```
Thr Phe Asp Tyr Pro Gly Arg Ala His Thr Phe Asp Asp Phe Cys Pro
1               5                   10                  15

Glu Cys Arg Ala Leu Gly Leu Gln Gly Cys Ala Phe Gln Ser Thr Val
                20                  25                  30

Ala Glu Leu Gln Arg Leu Lys Val Lys Val Gly Lys Thr Arg Glu Leu
                35                  40                  45
```

(2) INFORMATION FOR SEQ ID NO:15:

(i) SEQUENCE CHARACTERISTICS:
        (A) LENGTH: 327 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: SG3, BURMA, FIGURE 9

(xi) SEQUENCE DESCRIPTION: SEQ ID NO:15:

```
Gly Ala Asp Gly Thr Ala Glu Leu Thr Thr Thr Ala Ala Thr Arg Phe
1               5                   10                  15

Met Lys Asp Leu Tyr Phe Thr Ser Thr Asn Gly Val Gly Glu Ile Gly
                20                  25                  30

Arg Gly Ile Ala Leu Thr Leu Phe Asn Leu Ala Asp Thr Leu Leu Gly
                35                  40                  45

Gly Leu Pro Thr Glu Leu Ile Ser Ser Ala Gly Gly Gln Leu Phe Tyr
        50                  55                  60

Ser Arg Pro Val Val Ser Ala Asn Gly Glu Pro Thr Val Lys Leu Tyr
65                  70                  75                  80

Thr Ser Val Glu Asn Ala Gln Gln Asp Lys Gly Ile Ala Ile Pro His
                85                  90                  95

Asp Ile Asp Leu Gly Glu Ser Arg Val Val Ile Gln Asp Tyr Asp Asn
                100                 105                 110

Gln His Glu Gln Asp Arg Pro Thr Pro Ser Pro Ala Pro Ser Arg Pro
        115                 120                 125

Phe Ser Val Leu Arg Ala Asn Asp Val Leu Trp Leu Ser Leu Thr Ala
        130                 135                 140

Ala Glu Tyr Asp Gln Ser Thr Tyr Gly Ser Ser Thr Gly Pro Val Tyr
```

```
                  145                 150                 155                 160
Val Ser Asp Ser Val Thr Leu Val Asn Val Ala Thr Gly Ala Gln Ala
                165                 170                 175

Val Ala Arg Ser Leu Asp Trp Thr Lys Val Thr Leu Asp Gly Arg Pro
                180                 185                 190

Leu Ser Thr Ile Gln Gln Tyr Ser Lys Thr Phe Phe Val Leu Pro Leu
                195                 200                 205

Arg Gly Lys Leu Ser Phe Trp Glu Ala Gly Thr Thr Lys Ala Gly Tyr
                210                 215                 220

Pro Tyr Asn Tyr Asn Thr Thr Ala Ser Asp Gln Leu Leu Val Glu Asn
225                                 230                 235                 240

Ala Ala Gly His Arg Val Ala Ile Ser Thr Tyr Thr Thr Ser Leu Gly
                245                 250                 255

Ala Gly Pro Val Ser Ile Ser Ala Val Ala Val Leu Ala Pro His Ser
                260                 265                 270

Ala Leu Ala Leu Leu Glu Asp Thr Leu Asp Tyr Pro Ala Arg Ala His
                275                 280                 285

Thr Phe Asp Asp Phe Cys Pro Glu Cys Arg Pro Leu Gly Leu Gln Gly
                290                 295                 300

Cys Ala Phe Gln Ser Thr Val Ala Glu Leu Gln Arg Leu Lys Met Lys
305                                 310                 315                 320

Val Gly Lys Thr Arg Glu Leu
                325

(2) INFORMATION FOR SEQ ID NO:16:

(i) SEQUENCE CHARACTERISTICS:
        (A) LENGTH: 327 amino acids
        (B) TYPE: amino acid
        (D) TOPOLOGY: linear (ii) MOLECULE TYPE: protein (iii) HYPOTHETICAL: NO (vi) ORIGINAL SOURCE:
         (C) INDIVIDUAL ISOLATE: SG3, MEXICO, FIGURE 9

(xi) SEQUENCE DESCRIPTION: SEQ ID NO:16:

Gly Ala Asp Gly Thr Ala Glu Leu Thr Thr Thr Ala Ala Thr Arg Phe
1               5                   10                  15

Met Lys Asp Leu His Phe Thr Gly Leu Asn Gly Val Gly Glu Val Gly
                20                  25                  30

Arg Gly Ile Ala Leu Thr Leu Leu Asn Leu Ala Asp Thr Leu Leu Gly
            35                  40                  45

Gly Leu Pro Thr Glu Leu Ile Ser Ser Ala Gly Gln Leu Phe Tyr
    50                  55                  60

Ser Arg Pro Val Val Ser Ala Asn Gly Glu Pro Thr Val Lys Leu Tyr
65                  70                  75                  80

Thr Ser Val Glu Asn Ala Gln Gln Asp Lys Gly Val Ala Ile Pro His
                85                  90                  95

Asp Ile Asp Leu Gly Asp Ser Arg Val Val Ile Gln Asp Tyr Asp Asn
                100                 105                 110

Gln His Glu Gln Asp Arg Pro Thr Pro Ser Pro Ala Pro Ser Arg Pro
            115                 120                 125

Phe Ser Val Leu Arg Ala Asn Asp Val Leu Trp Leu Ser Leu Thr Ala
        130                 135                 140
```

```
Ala Glu Tyr Asp Gln Ser Thr Tyr Gly Ser Thr Gly Pro Val Tyr
145                 150                 155                 160

Ile Ser Asp Ser Val Thr Leu Val Asn Val Ala Thr Gly Ala Gln Ala
                165                 170                 175

Val Ala Arg Ser Leu Asp Trp Ser Lys Val Thr Leu Asp Gly Arg Pro
            180                 185                 190

Leu Pro Thr Val Glu Gln Tyr Ser Lys Thr Phe Phe Val Leu Pro Leu
            195                 200                 205

Arg Gly Lys Leu Ser Phe Trp Glu Ala Gly Thr Thr Lys Ala Gly Tyr
    210                 215                 220

Pro Tyr Asn Tyr Asn Thr Thr Ala Ser Asp Gln Ile Leu Ile Glu Asn
225                 230                 235                 240

Ala Ala Gly His Arg Val Ala Ile Ser Thr Tyr Thr Thr Arg Leu Gly
                245                 250                 255

Ala Gly Pro Val Ala Ile Ser Ala Ala Val Leu Ala Pro Arg Ser
            260                 265                 270

Ala Leu Ala Leu Leu Glu Asp Thr Phe Asp Tyr Pro Gly Arg Ala His
    275                 280                 285

Thr Phe Asp Asp Phe Cys Pro Glu Cys Arg Ala Leu Gly Leu Gln Gly
290                 295                 300

Cys Ala Phe Gln Ser Thr Val Ala Glu Leu Gln Arg Leu Lys Val Lys
305                 310                 315                 320

Val Gly Lys Thr Arg Glu Leu
                325

(2) INFORMATION FOR SEQ ID NO:17:

(i) SEQUENCE CHARACTERISTICS:
        (A) LENGTH: 436 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: C2, BURMA, FIGURE 9

(xi) SEQUENCE DESCRIPTION: SEQ ID NO:17:

Asn Ser Ile Thr Ser Thr Asp Val Arg Ile Leu Val Gln Pro Gly Ile
1               5                   10                  15

Ala Ser Glu Leu Val Ile Pro Ser Glu Arg Leu His Tyr Arg Asn Gln
                20                  25                  30

Gly Trp Arg Ser Val Glu Thr Ser Gly Val Ala Glu Glu Ala Thr
            35                  40                  45

Ser Gly Leu Val Met Leu Cys Ile His Gly Ser Leu Val Asn Ser Tyr
50                  55                  60

Thr Asn Thr Pro Tyr Thr Gly Ala Leu Gly Leu Leu Asp Phe Ala Leu
65                  70                  75                  80

Glu Leu Glu Phe Arg Asn Leu Thr Pro Gly Asn Thr Asn Thr Arg Val
                85                  90                  95

Ser Arg Tyr Ser Ser Thr Ala Arg His Arg Leu Arg Arg Gly Ala Asp
                100                 105                 110

Gly Thr Ala Glu Leu Thr Thr Thr Ala Ala Thr Arg Phe Met Lys Asp
            115                 120                 125

Leu Tyr Phe Thr Ser Thr Asn Gly Val Gly Glu Ile Gly Arg Gly Ile
            130                 135                 140
```

```
Ala Leu Thr Leu Phe Asn Leu Ala Asp Thr Leu Leu Gly Gly Leu Pro
145                 150                 155                 160

Thr Glu Leu Ile Ser Ser Ala Gly Gly Gln Leu Phe Tyr Ser Arg Pro
                165                 170                 175

Val Val Ser Ala Asn Gly Glu Pro Thr Val Lys Leu Tyr Thr Ser Val
            180                 185                 190

Glu Asn Ala Gln Gln Asp Lys Gly Ile Ala Ile Pro His Asp Ile Asp
            195                 200                 205

Leu Gly Glu Ser Arg Val Val Ile Gln Asp Tyr Asp Asn Gln His Glu
    210                 215                 220

Gln Asp Arg Pro Thr Pro Ser Pro Ala Pro Ser Arg Pro Phe Ser Val
225                 230                 235                 240

Leu Arg Ala Asn Asp Val Leu Trp Leu Ser Leu Thr Ala Ala Glu Tyr
                245                 250                 255

Asp Gln Ser Thr Tyr Gly Ser Ser Thr Gly Pro Val Tyr Val Ser Asp
            260                 265                 270

Ser Val Thr Leu Val Asn Val Ala Thr Gly Ala Gln Ala Val Ala Arg
    275                 280                 285

Ser Leu Asp Trp Thr Lys Val Thr Leu Asp Gly Arg Pro Leu Ser Thr
    290                 295                 300

Ile Gln Gln Tyr Ser Lys Thr Phe Phe Val Leu Pro Leu Arg Gly Lys
305                 310                 315                 320

Leu Ser Phe Trp Glu Ala Gly Thr Thr Lys Ala Gly Tyr Pro Tyr Asn
                325                 330                 335

Tyr Asn Thr Thr Ala Ser Asp Gln Leu Leu Val Glu Asn Ala Ala Gly
            340                 345                 350

His Arg Val Ala Ile Ser Thr Tyr Thr Thr Ser Leu Gly Ala Gly Pro
    355                 360                 365

Val Ser Ile Ser Ala Val Ala Val Leu Ala Pro His Ser Ala Leu Ala
    370                 375                 380

Leu Leu Glu Asp Thr Leu Asp Tyr Pro Ala Arg Ala His Thr Phe Asp
385                 390                 395                 400

Asp Phe Cys Pro Glu Cys Arg Pro Leu Gly Leu Gln Gly Cys Ala Phe
                405                 410                 415

Gln Ser Thr Val Ala Glu Leu Gln Arg Leu Lys Met Lys Val Gly Lys
            420                 425                 430

Thr Arg Glu Leu
        435

(2) INFORMATION FOR SEQ ID NO:18:

(i) SEQUENCE CHARACTERISTICS:
        (A) LENGTH: 435 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: C2, MEXICO, FIGURE 9

(xi) SEQUENCE DESCRIPTION: SEQ ID NO:18:

Asn Ser Ile Thr Ser Thr Asp Val Arg Ile Leu Val Gln Pro Gly Ile
1               5                   10                  15

Ala Ser Glu Leu Val Ile Pro Ser Glu Arg Leu His Tyr Arg Asn Gln
```

```
                    20                  25                  30
Gly Trp Arg Ser Val Glu Thr Ser Gly Val Ala Glu Glu Ala Thr
                35                  40                  45
Ser Gly Leu Val Met Leu Cys Ile His Gly Ser Pro Val Asn Ser Tyr
    50                  55                  60
Thr Asn Thr Pro Tyr Thr Gly Ala Leu Gly Leu Leu Asp Phe Ala Leu
65                  70                  75                  80
Glu Leu Glu Phe Arg Asn Leu Thr Thr Cys Asn Thr Asn Thr Arg Val
                85                  90                  95
Ser Arg Tyr Ser Ser Thr Ala Arg His Ser Ala Arg Gly Ala Asp Gly
                100                 105                 110
Thr Ala Glu Leu Thr Thr Thr Ala Ala Thr Arg Phe Met Lys Asp Leu
                115                 120                 125
His Phe Thr Gly Leu Asn Gly Val Gly Glu Val Gly Arg Gly Ile Ala
    130                 135                 140
Leu Thr Leu Leu Asn Leu Ala Asp Thr Leu Leu Gly Gly Leu Pro Thr
145                 150                 155                 160
Glu Leu Ile Ser Ser Ala Gly Gly Gln Leu Phe Tyr Ser Arg Pro Val
                165                 170                 175
Val Ser Ala Asn Gly Glu Pro Thr Val Lys Leu Tyr Thr Ser Val Glu
                180                 185                 190
Asn Ala Gln Gln Asp Lys Gly Val Ala Ile Pro His Asp Ile Asp Leu
                195                 200                 205
Gly Asp Ser Arg Val Val Ile Gln Asp Tyr Asp Asn Gln His Glu Gln
                210                 215                 220
Asp Arg Pro Thr Pro Ser Pro Ala Pro Ser Arg Pro Phe Ser Val Leu
225                 230                 235                 240
Arg Ala Asn Asp Val Leu Trp Leu Ser Leu Thr Ala Ala Glu Tyr Asp
                245                 250                 255
Gln Ser Thr Tyr Gly Ser Ser Thr Gly Pro Val Tyr Ile Ser Asp Ser
                260                 265                 270
Val Thr Leu Val Asn Val Ala Thr Gly Ala Gln Ala Val Ala Arg Ser
                275                 280                 285
Leu Asp Trp Ser Lys Val Thr Leu Asp Gly Arg Pro Leu Pro Thr Val
                290                 295                 300
Glu Gln Tyr Ser Lys Thr Phe Val Leu Pro Leu Arg Gly Lys Leu
305                 310                 315                 320
Ser Phe Trp Glu Ala Gly Thr Thr Lys Ala Gly Tyr Pro Tyr Asn Tyr
                325                 330                 335
Asn Thr Thr Ala Ser Asp Gln Ile Leu Ile Glu Asn Ala Ala Gly His
                340                 345                 350
Arg Val Ala Ile Ser Thr Tyr Thr Thr Arg Leu Gly Ala Gly Pro Val
                355                 360                 365
Ala Ile Ser Ala Ala Ala Val Leu Ala Pro Arg Ser Ala Leu Ala Leu
    370                 375                 380
Leu Glu Asp Thr Phe Asp Tyr Pro Gly Arg Ala His Thr Phe Asp Asp
385                 390                 395                 400
Phe Cys Pro Glu Cys Arg Ala Leu Gly Leu Gln Gly Cys Ala Phe Gln
                405                 410                 415
Ser Thr Val Ala Glu Leu Gln Arg Leu Lys Val Lys Val Gly Lys Thr
                420                 425                 430
Arg Glu Leu
    435
```

(2) INFORMATION FOR SEQ ID NO:19:

(i) SEQUENCE CHARACTERISTICS:
        (A) LENGTH: 660 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: ORF 2, BURMA, FIGURE 9

(xi) SEQUENCE DESCRIPTION: SEQ ID NO:19:

```
Met Arg Pro Arg Pro Ile Leu Leu Leu Leu Met Phe Leu Pro Met
1               5                   10                  15

Leu Pro Ala Pro Pro Gly Gln Pro Ser Gly Arg Arg Arg Gly Arg
            20                  25                  30

Arg Ser Gly Gly Ser Gly Gly Gly Phe Trp Gly Asp Arg Val Asp Ser
            35                  40                  45

Gln Pro Phe Ala Ile Pro Tyr Ile His Pro Thr Asn Pro Phe Ala Pro
50                  55                  60

Asp Val Thr Ala Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Val
            85                  90                  95

Ala Ser Arg Arg Arg Pro Thr Thr Ala Gly Ala Ala Pro Leu Thr Ala
            100                 105                 110

Val Ala Pro Ala His Asp Thr Pro Val Pro Asp Val Asp Ser Arg
            115                 120                 125

Gly Ala Ile Leu Arg Arg Gln Tyr Asn Leu Ser Thr Ser Pro Leu Thr
130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
            165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
            195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
            245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Leu Val Asn Ser Tyr
            275                 280                 285

Thr Asn Thr Pro Tyr Thr Gly Ala Leu Gly Leu Leu Asp Phe Ala Leu
            290                 295                 300

Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
```

```
                      325                 330                 335
Gly Thr Ala Glu Leu Thr Thr Ala Ala Thr Arg Phe Met Lys Asp
                340                 345                 350

Leu Tyr Phe Thr Ser Thr Asn Gly Val Gly Glu Ile Gly Arg Gly Ile
            355                 360                 365

Ala Leu Thr Leu Phe Asn Leu Ala Asp Thr Leu Leu Gly Gly Leu Pro
            370                 375                 380

Thr Glu Leu Ile Ser Ser Ala Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro His Asp Ile Asp
                420                 425                 430

Leu Gly Glu Ser Arg Val Val Ile Gln Asp Tyr Asp Asn Gln His Glu
                435                 440                 445

Gln Asp Arg Pro Thr Pro Ser Pro Ala Pro Ser Arg Pro Phe Ser Val
            450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
                485                 490                 495

Ser Val Thr Leu Val Asn Val Ala Thr Gly Ala Gln Ala Val Ala Arg
                500                 505                 510

Ser Leu Asp Trp Thr Lys Val Thr Leu Asp Gly Arg Pro Leu Ser Thr
            515                 520                 525

Ile Gln Gln Tyr Ser Lys Thr Phe Phe Val Leu Pro Leu Arg Gly Lys
            530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
                580                 585                 590

Val Ser Ile Ser Ala Val Ala Val Leu Ala Pro His Ser Ala Leu Ala
            595                 600                 605

Leu Leu Glu Asp Thr Leu Asp Tyr Pro Ala Arg Ala His Thr Phe Asp
            610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
            660

(2) INFORMATION FOR SEQ ID NO:20:

(i) SEQUENCE CHARACTERISTICS:
        (A) LENGTH: 659 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: ORF 2, MEXICO, FIGURE 9
```

(xi) SEQUENCE DESCRIPTION: SEQ ID NO:20:

```
Met Arg Pro Arg Pro Leu Leu Leu Phe Leu Leu Phe Leu Pro Met
1               5                   10                  15

Leu Pro Ala Pro Pro Thr Gly Gln Pro Ser Gly Arg Arg Gly Arg
                20                  25                  30

Arg Ser Gly Gly Thr Gly Gly Phe Trp Gly Asp Arg Val Asp Ser
            35                  40                  45

Gln Pro Phe Ala Ile Pro Tyr Ile His Pro Thr Asn Pro Phe Ala Pro
50                      55                  60

Asp Val Ala Ala Ala Ser Gly Ser Gly Pro Arg Leu Arg Gln Pro Ala
65                  70                  75                  80

Arg Pro Leu Gly Ser Thr Trp Arg Asp Gln Ala Gln Arg Pro Ser Ala
                85                  90                  95

Ala Ser Arg Arg Arg Pro Ala Thr Ala Gly Ala Ala Leu Thr Ala
            100                 105                 110

Val Ala Pro Ala His Asp Thr Ser Pro Val Pro Asp Val Asp Ser Arg
            115                 120                 125

Gly Ala Ile Leu Arg Arg Gln Tyr Asn Leu Ser Thr Ser Pro Leu Thr
        130                 135                 140

Ser Ser Val Ala Ser Gly Thr Asn Leu Val Leu Tyr Ala Ala Pro Leu
145                 150                 155                 160

Asn Pro Pro Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
290                 295                 300

Glu Leu Glu Phe Arg Asn Leu Thr Thr Cys Asn Thr Asn Thr Arg Val
305                 310                 315                 320

Ser Arg Tyr Ser Ser Thr Ala Arg His Ser Arg Gly Ala Asp Gly
            325                 330                 335

Thr Ala Glu Leu Thr Thr Thr Ala Ala Thr Arg Phe Met Lys Asp Leu
                340                 345                 350

His Phe Thr Gly Leu Asn Gly Val Gly Glu Val Gly Arg Gly Ile Ala
            355                 360                 365

Leu Thr Leu Leu Asn Leu Ala Asp Thr Leu Leu Gly Gly Leu Pro Thr
        370                 375                 380

Glu Leu Ile Ser Ser Ala Gly Gly Gln Leu Phe Tyr Ser Arg Pro Val
385                 390                 395                 400

Val Ser Ala Asn Gly Glu Pro Thr Val Lys Leu Tyr Thr Ser Val Glu
```

-continued

```
                    405                 410                  415
Asn Ala Gln Gln Asp Lys Gly Val Ala Ile Pro His Asp Ile Asp Leu
                420                 425                 430
Gly Asp Ser Arg Val Val Ile Gln Asp Tyr Asp Asn Gln His Glu Gln
                435                 440                 445
Asp Arg Pro Thr Pro Ser Pro Ala Pro Ser Arg Pro Phe Ser Val Leu
    450                 455                 460
Arg Ala Asn Asp Val Leu Trp Leu Ser Leu Thr Ala Ala Glu Tyr Asp
465                 470                 475                 480
Gln Ser Thr Tyr Gly Ser Ser Thr Gly Pro Val Tyr Ile Ser Asp Ser
                485                 490                 495
Val Thr Leu Val Asn Val Ala Thr Gly Ala Gln Ala Val Ala Arg Ser
                500                 505                 510
Leu Asp Trp Ser Lys Val Thr Leu Asp Gly Arg Pro Leu Pro Thr Val
                515                 520                 525
Glu Gln Tyr Ser Lys Thr Phe Phe Val Leu Pro Leu Arg Gly Lys Leu
                530                 535                 540
Ser Phe Trp Glu Ala Gly Thr Thr Lys Ala Gly Tyr Pro Tyr Asn Tyr
545                 550                 555                 560
Asn Thr Thr Ala Ser Asp Gln Ile Leu Ile Glu Asn Ala Ala Gly His
                565                 570                 575
Arg Val Ala Ile Ser Thr Tyr Thr Thr Arg Leu Gly Ala Gly Pro Val
                580                 585                 590
Ala Ile Ser Ala Ala Ala Val Leu Ala Pro Arg Ser Ala Leu Ala Leu
                595                 600                 605
Leu Glu Asp Thr Phe Asp Tyr Pro Gly Arg Ala His Thr Phe Asp Asp
                610                 615                 620
Phe Cys Pro Glu Cys Arg Ala Leu Gly Leu Gln Gly Cys Ala Phe Gln
625                 630                 635                 640
Ser Thr Val Ala Glu Leu Gln Arg Leu Lys Val Lys Val Gly Lys Thr
                645                 650                 655
Arg Glu Leu
```

(2) INFORMATION FOR SEQ ID NO:21:

(i) SEQUENCE CHARACTERISTICS:
        (A) LENGTH: 33 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: 406.4-2, BURMA, FIGURE 8

(xi) SEQUENCE DESCRIPTION: SEQ ID NO:21:

```
Ala Asn Pro Pro Asp His Ser Ala Pro Leu Gly Val Thr Arg Pro Ser
1               5                   10                  15
Ala Pro Pro Leu Pro His Val Val Asp Leu Pro Gln Leu Gly Pro Arg
                20                  25                  30
Arg
```

(2) INFORMATION FOR SEQ ID NO:22:

(i) SEQUENCE CHARACTERISTICS:
        (A) LENGTH: 33 amino acids

```
        (B) TYPE: amino acid
        (D) TOPOLOGY: linear (ii) MOLECULE TYPE: protein (iii) HYPOTHETICAL: NO (vi) ORIGINAL SOURCE:
         (C) INDIVIDUAL ISOLATE: 406.4-2, MEXICO, FIGURE 8

(xi) SEQUENCE DESCRIPTION: SEQ ID NO:22:

Ala Asn Gln Pro Gly His Leu Ala Pro Leu Gly Glu Ile Arg Pro Ser
1               5                   10                  15

Ala Pro Pro Leu Pro Pro Val Ala Asp Leu Pro Gln Pro Gly Leu Arg
            20                  25                  30

Arg
```